United States Patent
Nasir et al.

(10) Patent No.: US 11,887,707 B2
(45) Date of Patent: Jan. 30, 2024

(54) METHOD AND SYSTEM FOR MANAGING CHRONIC ILLNESS HEALTH CARE RECORDS

(71) Applicant: University of Central Florida Research Foundation, Inc., Orlando, FL (US)

(72) Inventors: Ayan Nasir, Orlando, FL (US); Varadraj Gurupur, Orlando, FL (US); Syed Usman Mumtaz, Windermere, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 228 days.

(21) Appl. No.: 17/104,023

(22) Filed: Nov. 25, 2020

(65) Prior Publication Data

US 2021/0098095 A1 Apr. 1, 2021

Related U.S. Application Data

(63) Continuation-in-part of application No. 16/988,190, filed on Aug. 7, 2020, which is a continuation of application No. 15/279,668, filed on Sep. 29, 2016, now Pat. No. 10,790,049.

(60) Provisional application No. 62/234,792, filed on Sep. 30, 2015.

(51) Int. Cl.
*G16H 10/60* (2018.01)

(52) U.S. Cl.
CPC ................... *G16H 10/60* (2018.01)

(58) Field of Classification Search
CPC ..................................................... G16H 10/60
See application file for complete search history.

(56) References Cited

U.S. PATENT DOCUMENTS

| 10,540,448 | B2 * | 1/2020 | Anand | ............... | G16H 50/20 |
| 2009/0271218 | A1 * | 10/2009 | Mok | ............... | G16H 70/20 |
| | | | | | 705/2 |
| 2011/0125531 | A1 * | 5/2011 | Seare | ............... | G06Q 10/00 |
| | | | | | 705/2 |

(Continued)

*Primary Examiner* — Rajesh Khattar
*Assistant Examiner* — Steven G. S. Sanghera
(74) *Attorney, Agent, or Firm* — Nicholas Pfeifer; Smith & Hopen, P. A.

(57) ABSTRACT

A method and system for managing health care patient record data including identifying and conveying recordation and temporal inconsistencies in health care patient data pertaining to chronic illnesses. An embodiment of the present invention includes identifying a first health care encounter date on which a chronic illness is recorded in a patient's digital health care data and determining if the chronic illness was recorded in the patient's digital health care data for each subsequent health care encounter. Some embodiments also identify the stage of the chronic illness at each encounter to determine if and how the condition of the chronic illness has changed. Some embodiments generate alerts to inform users when a preexisting chronic illness is not subsequently identified and/or if the subsequent diagnosis of the chronic illness indicates that the condition of the chronic illness has changed by some predetermined amount.

18 Claims, 21 Drawing Sheets

(56) References Cited

U.S. PATENT DOCUMENTS

2013/0152005 A1* 6/2013 McLaren ............... G16H 10/60
715/771
2016/0232324 A1* 8/2016 Liu ...................... A61B 5/4842

* cited by examiner

▸ Template

Last Name,First Name,DoB,Address,Phone #,Email,Ins Co,Ins Group #,Ins Policy #,Med History,Allergies,Weight,Height,Age,Race ▸ PatientForms P1,P1,2/22/54,Complete,8945217934,Complete,N/A,N/A,8495985914,Complete,N/A,292,77,57,Blue
P2,P2,7/17/64,Complete,9823286899,Complete,N/A,3354734688,9681255857,Complete,Complete, 315,56,47,N/A
P3,P3,6/16/85,Complete,9832107225,N/A,N/A,4085897516,N/A,Complete,Complete,214,84,26,Red
P4,P4,N/A,N/A,2486984588,Complete,Complete,N/A,9838891688,Complete,Complete,149,N/A,N/ A,Blue
P5,P5,N/A,N/A,Complete,8229701469,Complete,Complete,1978108556,1450221526,Complete,Complete, 135,N/A,N/A,N/A
P6,P6,6/18/86,Complete,9993450610,N/A,N/A,8932757385,6397254206,Complete,Complete, 187,62,25,N/A
P7,P7,6/14/80,Complete,1857758413,Complete,N/A,5774440050,N/A,N/A,N/A,135,N/A,2,N/A
P8,P8,N/A,Complete,1088205438,N/A,Complete,8561178035,7981797488,Complete,Complete,236,N/ A,N/A,Green
P9,P9,3/27/36,Complete,2148491160,N/A,Complete,7901815542,2054290177,Complete,Complete, 204,70,75,N/A
P10,P10,N/A,Complete,7198233887,Complete,Complete,7110963024,8140585368,Complete,Complete, 274,83,N/A,Red
P11,P11,11/26/04,Complete,N/A,Complete,N/A,7505800530,7371637729,Complete,Complete, 327,59,7,N/A
P12,P12,1/2/02,Complete,6936330182,Complete,Complete,1732265201,7362797720,Complete,N/A, 278,N/A,9,Orange
P13,P13,11/1/79,N/A,N/A,Complete,2082387399,N/A,Complete,Complete,
114,70,32,Violet
P14,P14,8/29/96,Complete,7558942144,Complete,Complete,8968736543,1589144199,N/A,Complete, 322,N/A,15,Red
P15,P15,6/21/90,N/A,1028723454,Complete,Complete,4672767433,N/A,Complete,Complete,245,N/A, 13,Violet
P16,P16,9/5/01,Complete,2535132600,Complete,Complete,N/A,4725240219,Complete,Complete, 268,82,18,Violet
P17,P17,3/3/77,Complete,4112531449,Complete,Complete.

Fig. 4

```
Result Print Out:
PDS using user IWs is: 83.44624910265614
PDS using balanced IWs is: 82.41200301307S2
No PSS generated.
No DFCS with subgroup generated.

RSS for each entry as follows:
Last Name:     First Name: P1    RSS: 78.57142857142857
Last Name:     First Name: P2    RSS: 86.60714285714286
Last Name:     First Name: P3    RSS: 83.92857142857143
Last Name:     First Name: P4    RSS: 67.41071428571429
Last Name:     First Name: P5    RSS: 74.55357142857143
Last Name:     First Name: P6    RSS: 82.14285714285714
Last Name:     First Name: P7    RSS: 62.94642857142857
Last Name:     First Name: P8    RSS: 75.44642857142857
Last Name:     First Name: P9    RSS: 90.17857142857143
Last Name:     First Name: P10   RSS: 82.14285714285714
Last Name:     First Name: P11   RSS: 79.46428571428571
Last Name:     First Name: P12   RSS: 88.83928571428571
Last Name:     First Name: P13   RSS: 81.25
Last Name:     First Name: P14   RSS: 88.83928571428571
Last Name:     First Name: P15   RSS: 86.16071428571429
Last Name:     First Name: P16   RSS: 85.53571428571429
Last Name:     First Name: P17   RSS: 100.0
Last Name:     First Name: P18   RSS: 88.83928571428571
Last Name:     First Name: P19   RSS: 71.875
Last Name:     First Name: P20   RSS: ...
```

Fig. 9

```
result.txt

Last Name:   P195   First Name:   P195   RSS: 80.0
Last Name:   P196   First Name:   P196   RSS: 60.0
Last Name:   P197   First Name:   P197   RSS: 86.6666666666667
Last Name:   P198   First Name:   P198   RSS: 86.6666666666667
Last Name:   P199   First Name:   P199   RSS: 93.3333333333333

DFCS for each field is as follows:
Last Name:      78.8944723618004
First Name:     100.0
DoB:            78.8944723618004
Address:        83.4170854271367
Phone #:        81.9095477386934
Email:          79.8994974874371
Ins Co:         80.4020100502513
Ins Group #:    83.4170854271367
Ins Policy #:   79.3969849246231
Med History:    77.3869346733668
Allergies:      76.8844221105528
Weight:         80.4020100502513
Height:         71.8592964824121
Age:            78.8944723618004
Race:           83.4170854271367
```

End of Report

Fig. 10

```
MRN, Age, Race, Visit Date, DX1, DX2, DX3, DX4
100001, 68, White, 9/10/15, N181, I5021, NA, NA
100354, 34, Latino, 6/8/18, I5030, NA, NA, NA
100001, 70, White, 9/6/17, N182, I5022, I495, NA
165389, 55, Asian, 11/3/13, I499, NA, NA, NA
```

```
Welcome to CCMP. Please enter the name of the patient data file.
demo.csv

Please enter the chronic conditions you would like to track.
CHF, CKD

Please enter any subpopulation criteria:
Race

Loading...
Report Complete.
```

```
CCMP Report:
Database CCMS: 97.567
Database CCGS: 84.342

Race CCMS for all chronic diagnoses:
White: 95.457
Black: 99.778
Latino: 93.332
Asian: 91.110
Native American: 94.330

CCMS/CCGS per chronic condition
CHF - 95.543 | NA
CKD - 96.665 | 84.342
DM  - 98.889 | NA Race CCMS per chronic diagnoses:
White: CHF 98.883, CKD 96.445, DM 94.436
Black: CHF 99.657, CKD 96.332, DM 91.178
Latino: CHF 92.267, CKD 99.567, DM 93.378
Asian: CHF 98.331, CKD 87.567, DM 100
Native American: CHF 94.446, CKD 95.553, DM 91.013

Combined CCMS per patient record
100001 - 95
100354 - 100
165389 - 100
```

Fig. 21

METHOD AND SYSTEM FOR MANAGING CHRONIC ILLNESS HEALTH CARE RECORDS

CROSS-REFERENCE TO RELATED APPLICATIONS

This nonprovisional application is a continuation-in-part of and claims priority to nonprovisional application Ser. No. 16/988,190, entitled "METHOD AND SYSTEM FOR MANAGING HEALTH CARE PATIENT RECORD DATA," filed Aug. 7, 2020 by the same inventor, which is a continuation of and claims priority to nonprovisional application Ser. No. 15/279,668, no U.S. Pat. No. 10,790,049, entitled "METHOD AND SYSTEM FOR MANAGING HEALTH CARE PATIENT RECORD DATA," filed Sep. 29, 2016 by the same inventor, which claims priority to U.S. provisional application 62/234,792 filed Sep. 30, 2015, the subject matter of which is incorporated by reference in its entirety.

BACKGROUND OF THE INVENTION

1. Field of the Invention

The present invention is directed to methods and systems for managing health care patient record data by evaluating the strength, completeness, and temporal accuracy of patient record data stored in health care/medical databases through determining the existence and relative quality of such data and performing statistical analyses.

2. Brief Description of the Prior Art

As health care moves into the 21st century, practitioners are moving into an era where traditionally qualitative methods of care are being complemented with quantitative research and analysis to better understand and solve various problems. To that end, one important problem health care practices currently face is the strength of their patient records and databases. While electronic records of patient information and care are now prevalent throughout health centers across the United States, there are few systems in place to ensure the completeness and validity of patient record data being stored. From basic information such as phone numbers or email addresses to more involved information such as family history and procedure records, there is no centralized mechanism by which data entered by health care staff can be checked for completeness and validity. Furthermore, there are no centralized mechanisms by which various health care software database packages and health center record-keeping measures can be compared to determine advantages and disadvantages of different systems.

Without having a mechanism that can identify strengths and shortcomings in record-keeping procedures it becomes more difficult to ensure the highest standard of care across health care centers. Most importantly, these problems are being uncovered at a time where data accuracy in health care is becoming a cornerstone for the burgeoning field of health informatics as well as a fundamental part of new models of health care practice. Accordingly, there is a continued need in the art for methods and systems that can identify strengths and shortcomings in record-keeping procedures for health care patient record data for the purpose of better and more accurate management of the patient record data. There is also a need for such a system that is independent of the health care platform used to store patient record data so that the system may be implemented by all health care providers across all health care platforms.

Database completeness information is also useful to identify health care disparities. The Department of Health and Human Services (DHHS) has found overwhelming evidence of health care disparity in minority groups, including disparities in care for cancer, cardiac disease, AIDS, asthma, and other illnesses. Research further shows that racial and ethnic disparities in health care exist even when insurance status, income, age, and severity of conditions are comparable. There is also evidence in health care decision making at multiple levels of bias against individuals based on age, creating health care disparity for the elderly. From a gender perspective, differences in health care expenditures and resource utilization lead to better quality of care among females. The underlying sources for these disparities are hard to identify. For example, a physician's assumption of literacy among patients disproportionately impacts minority patients, becoming a factor leading to disparity in care.

Research also points to social sources outside of interactions within the health care provider environment (such as neighborhood pressures, socioeconomic circumstances, education, segregation, impact on income, violence, and impact of segregation) contributing to real disparities in health care provided to minorities. These factors, often embedded and persistent historically, complicate the ability to determine tangible sources of disparities, ability to measure these sources' effects, and ability to create effective solutions to these sources of disparities. Within the provider context, "barriers in the patient-physician relationship contribute to racial disparities in the experience of health care." Furthermore, prejudice, clinical uncertainty (e.g. different interpretations of symptoms from minority patients), and stereotyping contribute as sources of health care disparity within the medical environment.

Analyzing patient record data in terms of variance between subpopulations is important clinically to determine areas of incomplete information and finding asymmetries that can be attributed to disparities in delivery of care. Current systems do not address the collection and maintenance of health care data with regard to identifying underlying disparities among various subpopulations, such as those based on age, gender, and race. Therefore, current systems fail at identifying and correcting underlying systemic issues causing these disparities. Accordingly, there is a need for a system that can identify variances in health care record completeness among subpopulations.

There is also a need to track chronic condition diagnoses in order to appropriately determine staging and management of chronic illnesses/conditions in an effort to improve the quality of health care and reduce health care costs. In the current era of medicine, chronic condition diagnoses and management has risen to the forefront of health care. Every step from the initial diagnosis to staging to treatment and monitoring are given careful attention to improve patient outcomes while suppressing related costs. The importance in communication among a multitude of relevant parties including the patient, providers, support staff, payers, health care institutions, administrators, and others establishes a need for a centralized system that can track and analyze chronic condition diagnoses and also notify users of inconsistencies in the diagnosis of these chronic illnesses. Specifically, it is crucial that these diagnoses are complete, consistent, and accurate. Currently, however, the health care industry lacks the necessary system and method to manage chronic condition diagnoses, which has led to an unacceptably low quality of health care delivery.

Moreover, Electronic Medical Records (EMR) are a vital component of the health care system, especially in utilization for patients with chronic medical conditions. With the many available EMR systems used in major health care systems, there lacks standardization for the way EMR data is categorized, processed, and retrieved. However, there have been recent developments in tools that have the ability to assess the completeness and strength of patient records for a given EMR.[2-3]

The approach needed to care for chronically ill patients is unique in that it requires ongoing monitoring and management rather than the originally designed acute intervention mode. EMRs are not always necessarily designed to provide a service that goes beyond the needs of an acute care system. It has been established that in order to meet the appropriate care standards for this patient population, clinical systems must be reconfigured accordingly.[4, 5] Although, EMR developers have evolved to meet this need, these systems are incapable of providing ongoing monitoring and management of chronic conditions.

Project (HCUP), which serves as a powerful source of data to increase the quality of health care research and care delivery.[11] Included in their family of databases, is a software tool known as the Beta Chronic Condition Indicator (CCI), which aims to simplify the process of assigning ICD codes for patients with chronic conditions. The tool works as an algorithm and automates the process by which chronic condition codes are assigned automatically based on the available information in the records.

Aside from the supplemental tools mentioned thus far, the current industry solutions for monitoring chronically ill patients using EMRs are limited. The major EMRs used typically have "supportive" features for chronic care management. This is limited to features such as care coordination, care team role assignment, and patient summary overviews. Features that serve to utilize patient data such as symptoms and vital signs to assist in monitoring are lacking. Below is Table 1, which provides a general overview of chronic care management features in commonly used EMRs.

TABLE 1

Chronic Care Management features in EMRs

| Cerner | eClinicalWorks | Allscripts | Practice Fusion |
|---|---|---|---|
| Longitudinal Record Design: Organized, summary view of a person's health and care story comprised of normalized data from disparate systems across care continuum | Chronic Care Management (CCM) Program: Enroll patients, assign care team roles, and provide care plans | Allscripts Chronic Care Management: A managed service that provides non face-to-face services for Medicare patients with two or more chronic conditions | Electronic Clinical Quality Measures: Track various aspects of patient care and improve performance of quality measures |

Providers especially rely on electronic records when caring for and monitoring patients with chronic medical conditions. While some EMRs have the ability to accommodate special parameters that are relevant to the specific conditions of these patients, there is still a need for features and organization in EMRs to provide the appropriate continuous care required for chronically ill patients. On the other hand, the literature is lacking regarding which disease parameters to continually measure for these patients.[6]

The idea of intersecting chronic care and technology has been theorized in one instance and is known as the eHealth Enhanced Chronic Care Model (eCCM).[7] It is proposed as a theoretical modification to the existing Chronic Care Model (CCM) based on a review of existing literature. The findings based on this model demonstrate the potential for an improved Chronic Care Model, but suggests that a complete feedback loop is required in order for technology to aid in care for the chronically ill. This means that providers must always be in direct communication with their patients, without relying significantly on other mediums to obtain information relevant to care.[8]

An area relevant to the design that caters towards management of this patient population is regarding the use of portals or personal health records (PHR).[9,10] This serves as an opportunity for patients to become engaged in their care outside of their visit by using an online platform. These platforms often have features that allow patients to access their records, schedule appointments, or provide medical updates to their providers.

A useful tool for the categorization of chronic conditions has been developed as part of the Health Cost and Utilization One particular feature found in the EMR Practice Fusion is a big step towards automated chronic care monitoring. The feature, named Electronic Clinical Quality Measures, is a customizable way to assign diagnostic codes to conditions based on how they are recorded into the chart and also serves as a tool that predicts outcomes. This type of feature allows providers to have a higher quality of documentation for their chronic patients. However, the health care industry needs a tool that can track chronic condition diagnoses in terms of completeness, consistency, and accuracy relative to established guidelines.

To the extent that specific patents/publications/products are discussed above in this Description of the Related Art Section or elsewhere in this application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

The disclosure is directed to inventive methods and systems for managing health care patient record data by evaluating the strength and completeness of patient record data stored in health care/medical databases through determining the existence and relative quality of such data and performing statistical analyses. An embodiment can include, but is not limited to, a method and system that is configured to (i) associate native health care patient record data of at least a first patient representing the first patient's health care record stored in a database to a plurality of data fields (or other type of organization), and examine the patient record data associated with the particular fields, (ii) assign a relative importance weight score to each of the plurality of data fields representing the first patient's health care patient record data, and (iii) generate statistical results that can be used to determine the completeness of individual patient record data as well as the general thoroughness of record keeping in a medical database. An embodiment can use a component that can be customized to the settings of the particular software package used for storing the patient record data, as well as a Comma Separated Values (CSV) file parser to develop and read concept maps.

Such a system (or tool), along with its various embodiments, can be called the Data Completeness Analysis Package (DCAP), which is a term used in this disclosure. This tool can either reside on an individual workstation or an accessible server, each of which can be separate from and/or directly connected to a health care database (and can also reside on a health care database itself). This tool was developed based on the following objectives: develop a tool that can be used alongside and be compatible with a variety of health care database software packages to automatically determine the completeness of individual patient records as well as aggregate patient records across health care centers and subpopulations; equip the tool with robust statistical analysis techniques to ensure that the importance of the various types of data is accounted for; and make the tool user friendly for health care staff to evaluate the strength of record-keeping. Based on these objectives, the tool created was successful in applying the statistical techniques evaluated and described in this disclosure and was able to evaluate the strength of an actual health care database (specifically, the HCUP SID Florida database), as described below.

According to an aspect, a method for managing health care patient record data includes the steps of: associating, by a processor, native health care patient record data of a first patient stored in a database to a plurality of data fields, wherein the native health care patient record data of the first patient represents the first patient's health care record; assigning, by a processor, a relative importance weight score to each of the plurality of data fields; and generating, by a processor, a record strength score of the first patient's health care record based on the relative importance weight score assignments.

According to an embodiment, the step of generating further comprises the step of determining a record strength score pursuant to the following formula:

$$RSS(\%) = \frac{(IW_1)(X_1) + (IW_2)(X_2) + (IW_3)(X_3) + \ldots + (IW_n)(X_n)}{\sum_{i=1}^{n} IW_i} \times 100$$

where RSS=record strength score (total strength of completeness for the first patient's health care record constrained from 0 to 100%); IWi=importance weight of $i^{th}$ data field; and Xi=binary completeness variable for $i^{th}$ data field (1 represents complete data field, 0 represents incomplete).

According to an another aspect, a non-transitory computer-readable storage medium containing program code includes: program code for associating native health care patient record data of a first patient stored in a database to a plurality of data fields, wherein the native health care patient record data of the first patient represents the first patient's health care record; program code for assigning a relative importance weight score to each of the plurality of data fields; and program code for generating a record strength score of the first patient's health care record based on the relative importance weight score assignments.

According to an embodiment, the program code for generating further comprises program code for determining a record strength score pursuant to the following formula:

$$RSS(\%) = \frac{(IW_1)(X_1) + (IW_2)(X_2) + (IW_3)(X_3) + \ldots + (IW_n)(X_n)}{\sum_{i=1}^{n} IW_i} \times 100$$

where RSS=record strength score (total strength of completeness for the first patient's health care record constrained from 0 to 100%); IWi=importance weight of $i^{th}$ data field; and Xi=binary completeness variable for $i^{th}$ data field (1 represents complete data field, 0 represents incomplete).

An embodiment of the present invention includes a method for identifying and conveying recordation and temporal inconsistencies in health care patient data pertaining to chronic illnesses. The method comprises accessing a digital database using one or more processors, wherein the digital database includes a patient's digital health care data; identifying a chronic illness in the patient's digital health care data; identifying a first health care encounter in which the chronic illness was recorded in the patient's digital health care data; and determining a recorded stage of the chronic illness as diagnosed in the first encounter and recorded in the patient's digital health care data. The stage of the chronic illness resides on a clinical continuum of the progression of the chronic illness.

The method further includes identifying subsequent health care encounters and determining if the chronic illness was recorded in the patient's digital health care data for each subsequent health care encounter. If the chronic illness was not recorded in the patient's digital health care data for each subsequent health care encounter, the method includes generating an incompleteness alert, thereby informing a user that the patient's digital health care data is incomplete. If the chronic illness was recorded in the patient's digital health care data for each subsequent health care encounter, the method includes determining each stage of the chronic illness as diagnosed during each subsequent health care encounter and recorded in the patient's digital health care data.

Then, the method includes determining if the stage of the chronic illness diagnosed for each subsequent health care encounter has changed more than one stage along the clinical continuum in comparison to stages diagnosed for each prior health care encounter. If the stage of the chronic illness diagnosed for each subsequent health care encounter has changed more than one stage along the clinical continuum in comparison to stages diagnosed for each prior health care encounter, the method includes generating a temporal inconsistency alert. As a result, the user is informed that the patient's digital health care data is temporally inconsistent with the clinical continuum of the progression of the chronic illness.

In some embodiments, the method further includes digitally transforming the patient's digital health care data from a native format of one or more electronic medical records platforms into a standardized format.

Some embodiments of the method include calculating a chronic condition mapping score according to the following formula:

$$\text{Chronic Condition Mapping Score} = \frac{\sum_{1}^{N} B_i}{N} \times 100$$

where N is the total number of patient encounters since the chronic illness was first recorded, $B_i$ is a binary variable for patient encounter i. $B_i=1$ if the chronic illness is recorded and 0 if the chronic illness is not recorded during an encounter. The method further includes displaying on the graphic user interface the numerical chronic condition mapping score of the patient's digital health care record, thereby conveying a quantitative analysis of a completeness of the first patient's health care record pertaining to the chronic illness.

In some embodiments, the step of identifying the chronic illness in the patient's digital health care data includes identifying a diagnosis code recorded in the patient's digital health care data, accessing a database of diagnosis codes, and determining which chronic illness in the database of diagnosis codes corresponds to the diagnosis code recorded in the patient's digital health care data.

In some embodiments, the step of determining the stage of the chronic illness includes retrieving objective quantitative data of the chronic illness as recorded in the patient's digital health care data; accessing a digital chronic condition matrix, wherein the chronic condition matrix includes various stages of the chronic illness with each stage categorized by a range of objective numerical data. The method further includes determining which stage corresponds to the retrieved objective quantitative data in the patient's digital health care data.

In some embodiments, the stage of the chronic illness is determined by a recorded stage of the chronic illness and the clinical continuum of the progression of the chronic illness includes a plurality of stages arranged on a scale from a healthiest to a least healthiest stage. In some embodiments, the stage of the chronic illness is determined by objective quantitative data of the chronic illness and the clinical continuum of the progression of the chronic illness includes objective quantitative data. In some embodiments, the stage of the chronic illness is determined by objective textual data of the chronic illness and the clinical continuum of the progression of the chronic illness includes objective textual data.

In some embodiments, the step of generating a temporal inconsistency alert occurs if the stage of the chronic illness diagnosed for each subsequent health care encounter is not equal to or not progressively worse on the clinical continuum in comparison to stages diagnosed for each prior health care encounter.

An embodiment of the present invention includes a method for identifying and conveying recordation and temporal inconsistencies in health care patient data pertaining to chronic illnesses that includes the steps of accessing a digital database using one or more processors; identifying a diagnosis code recorded in the patient's digital health care data; digitally accessing a database of diagnosis codes, wherein the database of diagnosis codes includes a list of chronic illnesses corresponding to a list of diagnosis codes; determining the chronic illness corresponding to diagnosis code recorded in the patient's digital health care data; identifying a first health care encounter date on which the chronic illness was recorded in the patient's digital health care data; identifying subsequent health care encounters and determining if the chronic illness was recorded in the patient's digital health care data for each subsequent health care encounter; and if the chronic illness was not recorded in the patient's digital health care data for each subsequent health care encounter, generating and sending an incompleteness alert to a user, thereby informing the user that the patient's digital health care data is incomplete.

In some embodiments, the method includes digitally transforming the patient's digital health care data from a native format of one or more electronic medical records platforms into a standardized format.

some embodiments, further include calculating a chronic condition mapping score according to the following formula:

$$\text{Chronic Condition Mapping Score} = \frac{\sum_{1}^{N} B_i}{N} \times 100$$

where N is the total number of patient encounters since the chronic illness was first recorded, $B_i$ is a binary variable for patient encounter i. $B_i=1$ if the chronic illness is recorded and 0 if the chronic illness is not recorded during an encounter. The method also includes displaying on the graphic user interface the numerical chronic condition mapping score of the patient's digital health care record, thereby conveying a quantitative analysis of a completeness of the first patient's health care record pertaining to the chronic illness.

Some embodiments further include the steps of determining a recorded stage of the chronic illness as diagnosed in the first encounter and recorded in the patient's digital health care data, wherein the stage of the chronic illness resides on a clinical continuum of stages coinciding with the progression of the chronic illness. If the chronic illness was recorded in the patient's digital health care data for each subsequent health care encounter, the present invention determines each stage of the chronic illness as diagnosed during each subsequent health care encounter and recorded in the patient's digital health care data.

Some embodiments further include the steps of determining if the stage of the chronic illness diagnosed for each subsequent health care encounter has changed more than one stage along the clinical continuum in comparison to stages diagnosed for each prior health care encounter. If the stage of the chronic illness diagnosed for each subsequent health care encounter has changed more than one stage along the clinical continuum in comparison to stages diagnosed for each prior health care encounter, the present invention generates a temporal inconsistency alert, thereby informing the user that the patient's digital health care data is temporally inconsistent with the clinical continuum of the progression of the chronic illness.

In some embodiments, the step of determining the stage of the chronic illness includes retrieving objective quantitative data of the chronic illness as recorded in the patient's digital health care data; accessing a digital chronic condition matrix, wherein the chronic condition matrix includes various stages of the chronic illness with each stage categorized by a range of objective numerical data; and determining which stage corresponds to the retrieved objective quantitative data in the patient's digital health care data.

In some embodiments, the stage of the chronic illness is determined by a recorded stage of the chronic illness and the clinical continuum of the progression of the chronic illness includes a plurality of stages. In some embodiments, the stage of the chronic illness is determined by objective quantitative data of the chronic illness and the clinical continuum of the progression of the chronic illness includes objective quantitative data. In some embodiments, the stage of the chronic illness is determined by objective textual data of the chronic illness and the clinical continuum of the progression of the chronic illness includes objective textual data.

In some embodiments, the present invention includes a non-transitory computer-readable storage medium containing program code for executing the steps of providing remote access to a database over a network through a graphical user interface, wherein a patient's digital health care data can be stored in a native format dependent on a software platform used by the user; accessing, by one or more processors, the database containing the patient's digital health care data; transforming the patient's digital health care data from the native format into a standardized format; identifying a diagnosis code recorded in the patient's digital health care data; digitally accessing a database of diagnosis codes, wherein the database of diagnosis codes includes a list of chronic illnesses corresponding to a list of diagnosis codes; determining a chronic illness corresponding to the diagnosis code recorded in the patient's digital health care data; identifying a first health care encounter date on which the chronic illness was recorded in the patient's digital health care data; identifying subsequent health care encounters and determining if the chronic illness was recorded in the patient's digital health care data for each subsequent health care encounter; and if the chronic illness was not recorded in the patient's digital health care data for each subsequent health care encounter, generating and sending an incompleteness alert to a user, thereby informing the user that the patient's digital health care data is incomplete.

Some embodiments of the non-transitory computer-readable storage medium further include program coding for executing the steps of determining a recorded stage of the chronic illness as diagnosed in the first encounter and recorded in the patient's digital health care data, wherein the stage of the chronic illness resides on a clinical continuum of stages coinciding with the progression of the chronic illness; if the chronic illness was recorded in the patient's digital health care data for each subsequent health care encounter, determining each stage of the chronic illness as diagnosed during each subsequent health care encounter and recorded in the patient's digital health care data; determining if the stage of the chronic illness diagnosed for each subsequent health care encounter has changed more than one stage along the clinical continuum in comparison to stages diagnosed for each prior health care encounter; and if the stage of the chronic illness diagnosed for each subsequent health care encounter has changed more than one stage along the clinical continuum in comparison to stages diagnosed for each prior health care encounter, generating a temporal inconsistency alert, thereby informing the user that the patient's digital health care data is temporally inconsistent with the clinical continuum of the progression of the chronic illness.

Some embodiments of the non-transitory computer-readable storage medium further include program coding for executing the steps of retrieving objective quantitative data of the chronic illness as recorded in the patient's digital health care data; accessing a digital chronic condition matrix, wherein the chronic condition matrix includes various stages of the chronic illness with each stage categorized by a range of objective numerical data; and determining which stage corresponds to the retrieved objective quantitative data in the patient's digital health care data.

In accordance with a particularly advantageous aspect, a specialized improved computer system is created as described herein—in some embodiments the devices, databases and/or systems that are specifically structured, configured, connected, and/or programmed to evaluate the strength and completeness of patient record data stored in health care/medical databases through determining the existence and relative quality of such data and performing statistical analyses. In some embodiments the devices, databases and/or systems that are specifically structured, configured, connected, and/or programmed to evaluate the strength, completeness, and consistency of patient record data, related to chronic illnesses, stored in health care/medical databases through determining the existence and relative quality of such data and performing statistical analyses.

The transmission/transfer of data to/from systems, databases, engines, mobile devices, or other computer based devices/systems described in this disclosure can be via wireless communication/transmission over a network, which can be any suitable wired or wireless network capable of transmitting communication, including but not limited to a telephone network, Internet, Intranet, local area network, Ethernet, online communication, offline communications, wireless communications and/or similar communications means. The wireless transmission can be accomplished through any wireless protocol/technology, including, but not limited to, ZigBee standards-based protocol, Bluetooth technology, and/or Wi-Fi technology. Further, this data can be encrypted as needed based on the sensitivity of the data or the location the database with respect to a mobile device, for example. One system can be located in the same room, in a different room in the same building, in a completely different building and location from another system, or in the "cloud." The storage of the data in the cloud can be subject to security measures, as should be appreciated by those of skill in the art. Various alerts and notifications can be sent to authorized users of the systems described herein by the data transmission means described herein or as may be known or appreciated by those of skill in the art.

The details of one or more embodiments are described below and in the accompanying drawings. Other objects and advantages of the present invention will in part be obvious, and in part appear hereinafter.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which:

FIG. 4 is a representation of a sample CSV document in accordance with an embodiment.

FIG. 9 is a representation of a hypothetical patient DCAP result part 1 document in accordance with an embodiment.

FIG. 10 is a representation of a hypothetical patient DCAP result part 2 document in accordance with an embodiment.

FIG. 21 shows a sample results page with metrics.

Figure 1:
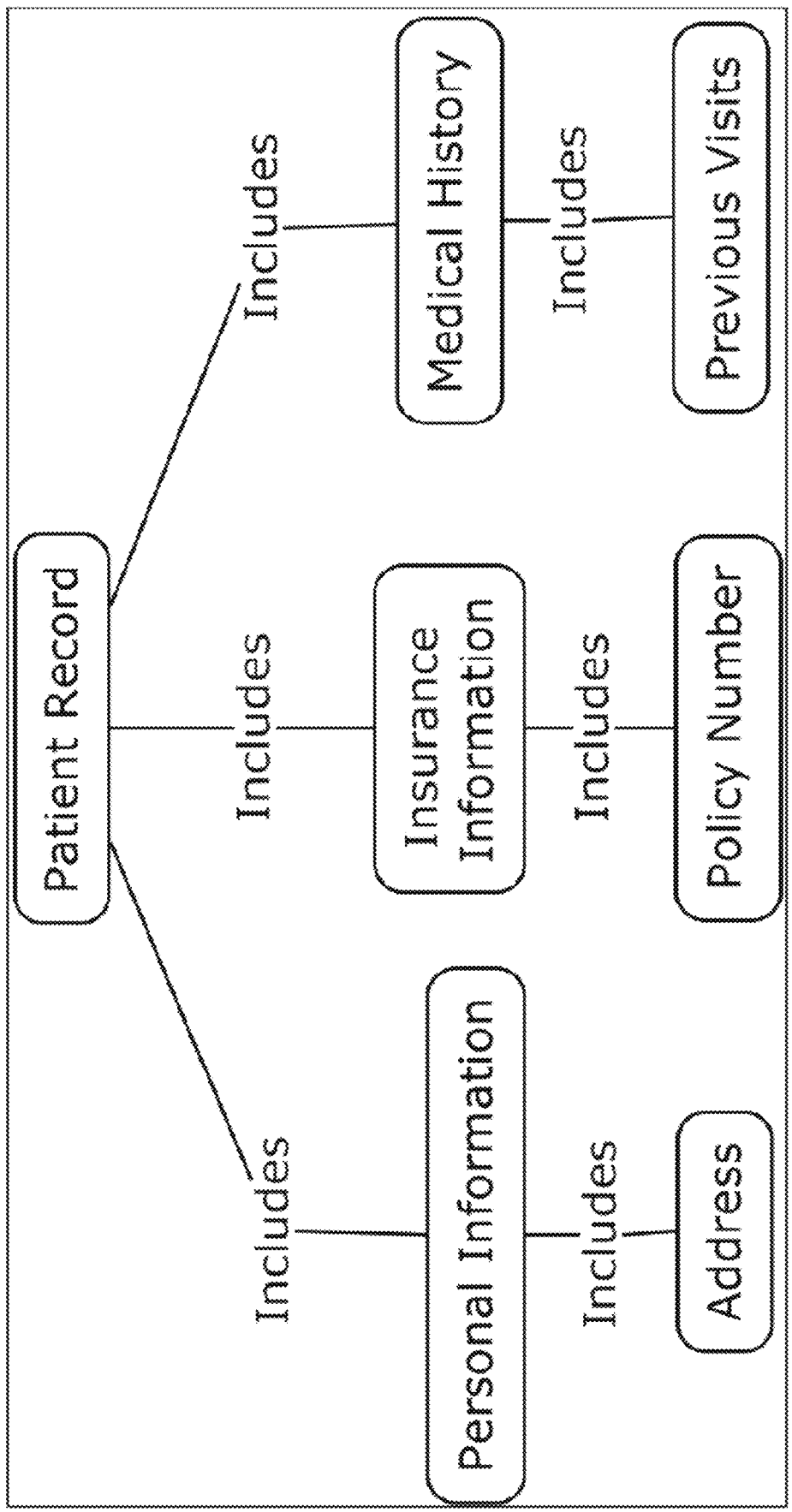
FIG. 1 is a schematic representation of a top level patient concept map in accordance with an embodiment.

Where applicable, like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION OF THE INVENTION

The present invention will be more fully understood and appreciated by reading the following Detailed Description in conjunction with the accompanying drawings, wherein like reference numerals refer to like components.

As detailed herein, the present disclosure is directed to embodiments of a method and system for managing health care patient record data by evaluating the strength and completeness of patient record data stored in health care/medical databases through determining the existence and relative quality of such data and performing statistical analyses. Some embodiments of the present invention are adapted to manage chronic illness health care records, the details of which are described in greater detail in the "managing chronic illness health care records" section below.

Patient record data includes but is not limited to electronic medical records (EMRs), electronic health records (EHRs), and any other type of digitized charts of a health care provider or collection of a patient's records.

As part of the proof of concept of embodiments described herein, but in no way limiting the embodiments described herein in any way, health care patient record data can be transformed into concept maps and these maps can be used as the basis for thorough statistical analysis. Concept maps are visual representations of data stored in a system, traditionally used for expressing knowledge in both a declarative and procedural sense. While most concept mapping tools have been used to express knowledge in a teaching environment to evaluate student learning of various topics, for the purposes of this disclosure, concept mapping is used as a schema through which patient record data stored could be represented and uniformly examined independent of the platform the data was originally stored on or other health care protocols that may make cross examinations of data sets more difficult. These concept maps can be developed through DCAP and then converted to CSV files. The CSV files can then be analyzed through a parser that allows the user to determine the strength of both individual patient records as well as the strength of record keeping throughout a particular database.

Some embodiments may use other known techniques for mapping or converting/transforming stored patient record data from the data's proprietary format based on a particular EMR or database into a standardized format. By standardizing the patient record data, the present invention becomes applicable across many different proprietary EMRs or databases and allows for cross-platform comparisons.

A premise of the proof of concept of the method and system described herein is to use concept maps as a representation of patient record data, although the patient record data can be represented in any manner as may be understood and/or appreciated by one of skill in the art. Referring now to FIG. 1, there is shown a schematic representation of a top level patient concept map in accordance with an embodiment. While traditionally concept maps are used to understand the knowledge set and complexity of a human learner, in the embodiment shown in FIG. 1, concept mapping is applied to represent patient information. This patient concept map is generated using data stored in the health care database and mapped using a user-developed "master map."

Figure 2:
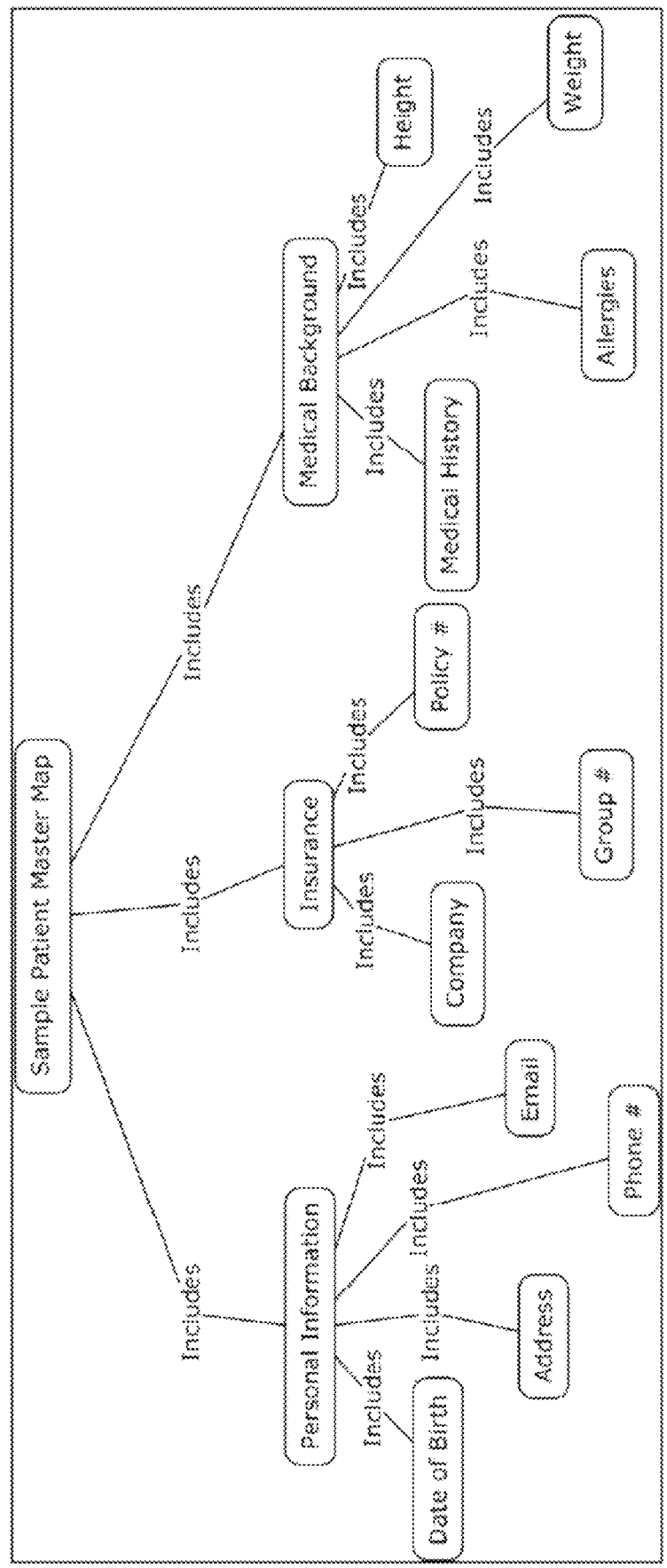
FIG. 2 is a schematic representation of a patient master map in accordance with an embodiment.

Referring now to FIG. 2, there is shown a schematic representation of a patient master map in accordance with an embodiment of the present invention. In FIG. 2, the master map is a schema that represents all the information, both the data fields and the proper interconnectedness amongst those data fields, the way the user wishes them to be stored in order to be considered "complete." While among patient records within a health care center this master map may be constrained by the database software used or methods of patient data recording used by staff, when comparing data sets from various health care centers using DCAP, the master map can be broadened as may be desired or necessary.

Figure 3:
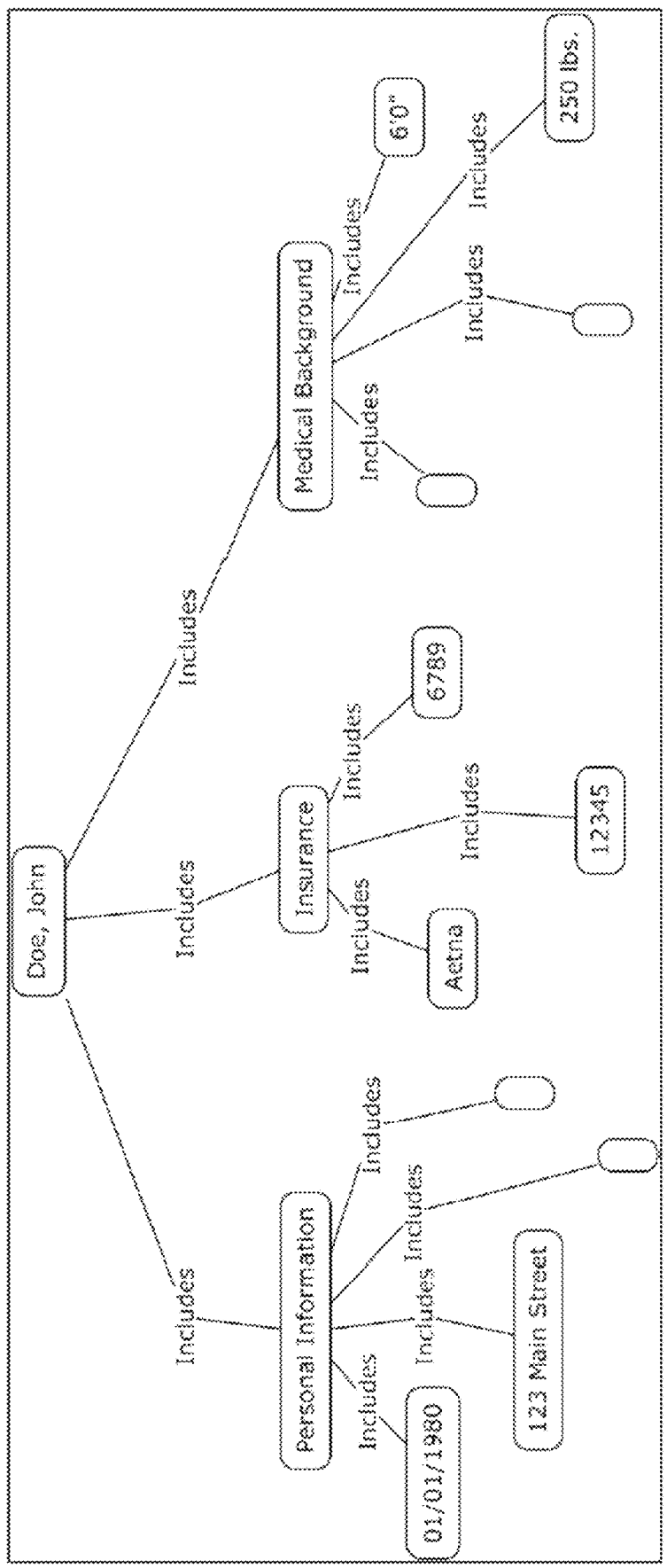
FIG. 3 is a schematic representation of a patient concept map with missing entries in accordance with an embodiment.

Referring now to FIG. 3, there is shown a schematic representation of a patient concept map with missing entries in accordance with an embodiment. The example of the master map shown in FIG. 3, a sample patient concept map with missing entries, i.e., not complete, and the example of a patient master map shown in FIG. 2 highlight how the concept of completeness and subsequently the strength of individual and aggregate patient data can be visualized. While FIGS. 2 and 3 are not comprehensive, they show how uniform concept map representations can serve as a platform through which basic shortcomings in patient data can be understood. It is also important to note that while cross subgroup relationships and other schema complexity may be useful in both traditional educational applications and even patient record applications. For example, address and phone number are concepts that can be linked to both personal information and billing information. For the purposes of this disclosure, having the information as defined by the master map can be sufficient to determine completeness.

Once the native patient data in a particular health care database software package is converted into concept map representations using a template master map, the concept maps are converted into CSV documents. Referring to FIG. 4, a sample CSV document is shown which includes concept labels, i.e., patient data fields. A CSV analyzer then parses the documents to see which fields are filled and unfilled, and then sends its results for statistical analysis. After the relevant statistics have been generated, e.g., individual patient records, entire database completeness, etc., a user-friendly interface system is used to display the results for the user.

Figure 5:
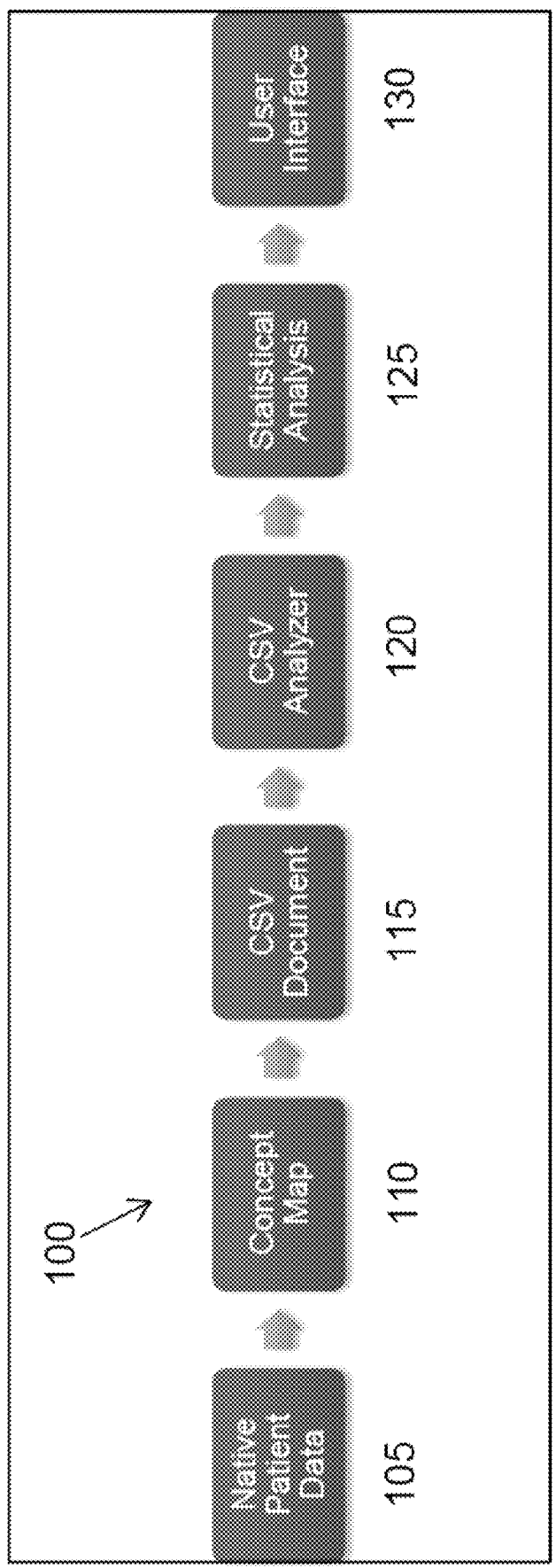
FIG. 5 is a flow chart of a method for managing health care patient record data in accordance with an embodiment.

Referring to FIG. 5, a flowchart of a basic method 100 for managing health care patient record data is provided based on the above description, in accordance with an embodiment. Each of the steps of the method can be carried out by a processor associated with DCAP and programmed/configured to carry out such steps.

Turing to step 105 of method 100, native patient record data is stored in at least one health care database with a particular software package and platform used for storing the patient record data. Other health care databases can exist, which store patient record data, and can include the same or a different software package and platform used for storing the patient record data.

The distinct software packages and platforms can make it difficult to relate information between different packages and platforms. Thus, some embodiments of the invention include steps for transforming the native data into a standardized format. The standardized format can include the health care patient data represented as a plurality of parsed data fields. In some embodiments, the transformation is based on concept maps as explained further below.

At step 110 of the method 100, a master map is developed that represents all the information, both the data fields and the proper interconnectedness amongst those data fields the way a user wishes them to be stored in order to be considered "complete." A concept map of stored native patient data of a particular patient, or concept maps, each of which is associated with particular patients, is generated using the developed master map as a template.

At step 115 of the method 100, each concept map is converted into a Comma Separated Values (CSV) document. This conversion to a CSV document is performed so that, at step 120 of the method 100, a CSV analyzer can analyze and parse the CSV document(s) to determine which data fields are filled and unfilled. At step 125 of the method 100, the results of the CSV analysis are statistically analyzed. At step 130 of the method 100, results of the statistical analysis are generated and transmitted and displayed to a user on any mobile or non-mobile computing device, for example. Further details of the statistical analysis are set forth in further detail below.

Advantages of embodiments, as briefly detailed above and shown in the Figures, are illustrated by the following Exemplary System, Uses and Functionalities description. However, the particular components, uses, functionalities and amounts thereof recited in this description, as well as other conditions and details, are to be interpreted to apply broadly in the art and should not be construed to unduly restrict or limit the invention in any way.

In accordance with an exemplary embodiment, once the patient data has been processed by the CSV analyzer or otherwise is associated with a plurality of data fields or other organization means, DCAP is programmed and/or configured to implement statistical analysis in order to determine the completeness and strength of the patient data. While completeness in each individual data field can be identifiable by the presence or lack of data, holistically analyzing an individual patient's record or an entire database or subgroup of patients can require determining which data fields are more important than others. With this in mind, DCAP generates a Record Strength Score (RSS) that is based upon user and/or computer determined input of Importance Weights (IW).

To illustrate this concept, a first example is a scenario where each data field holds an equivalent importance and thus equivalent IWs. A second example is a scenario where the IWs are different. For the scoring itself, each IW ranges from 1 to 100 points, with 100 denoting maximum importance. However, any number range can be used. For a record with all data fields of equivalent importance, 100 points are used for each data field. It is also important to note that while the concept map shows various grouping concepts that organizes the data fields, such as 'personal information', 'insurance', or 'medical background', these groupings have no scoring. Thus, the only scoring concepts are those with actual corresponding data fields. The scoring equation is as follows:

$$RSS(\%) = \frac{(IW_1)(X_1) + (IW_2)(X_2) + (IW_3)(X_3) + \ldots + (IW_n)(X_n)}{\sum_{i=1}^{n} IW_i} \times 100 \quad (1)$$

RSS is the Record Strength Score (Total Strength of Completeness for Individual Patient Record constrained from 0 to 100%); IWi is the Importance Weight of $i^{th}$ data field; Xi is the Binary Completeness Variable for $i^{th}$ data field (1 represents complete data field, 0 represents incomplete).

Figure 6:
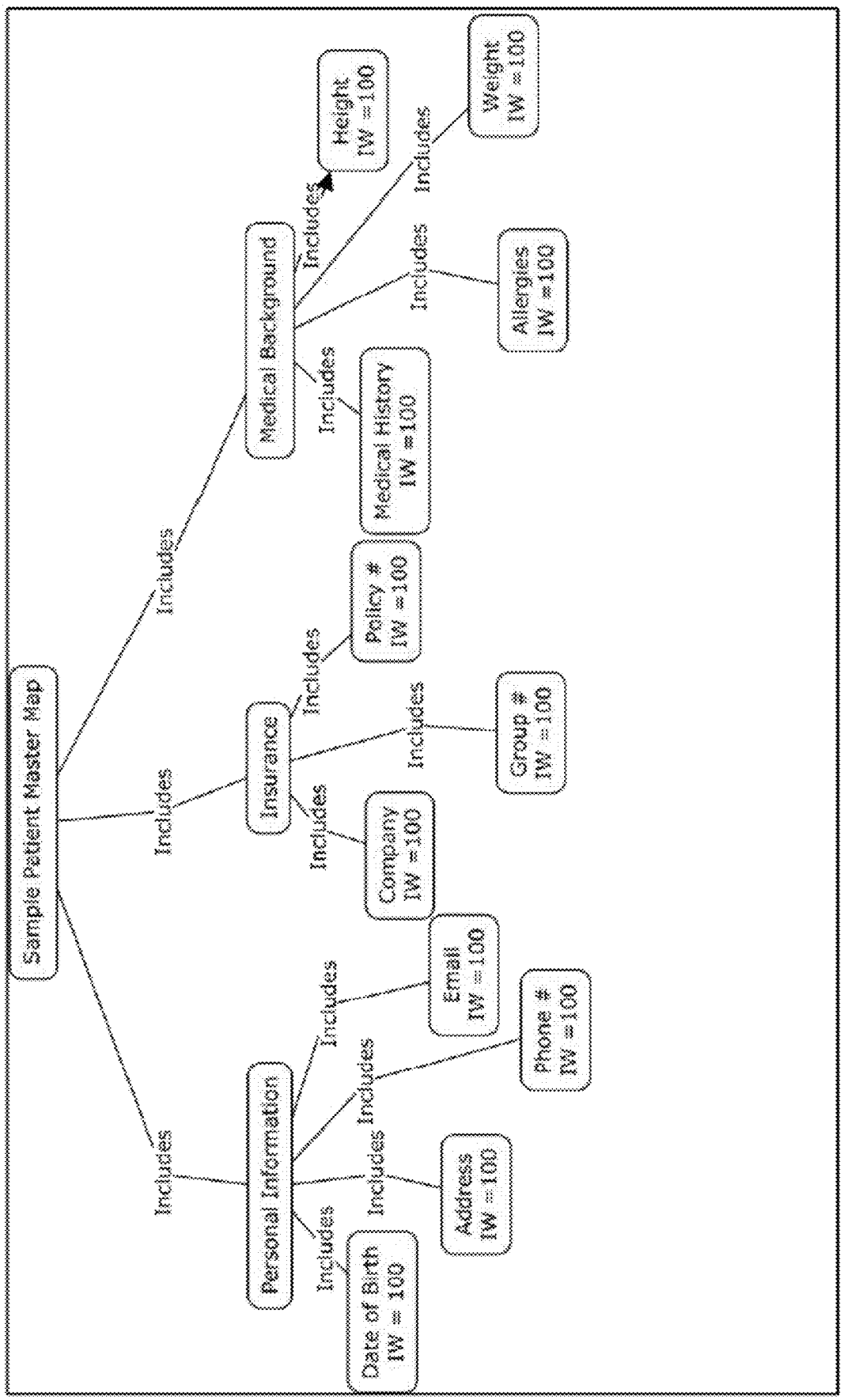
FIG. 6 is a schematic representation of a patient master map with balance scoring in accordance with an embodiment.
Figure 7:
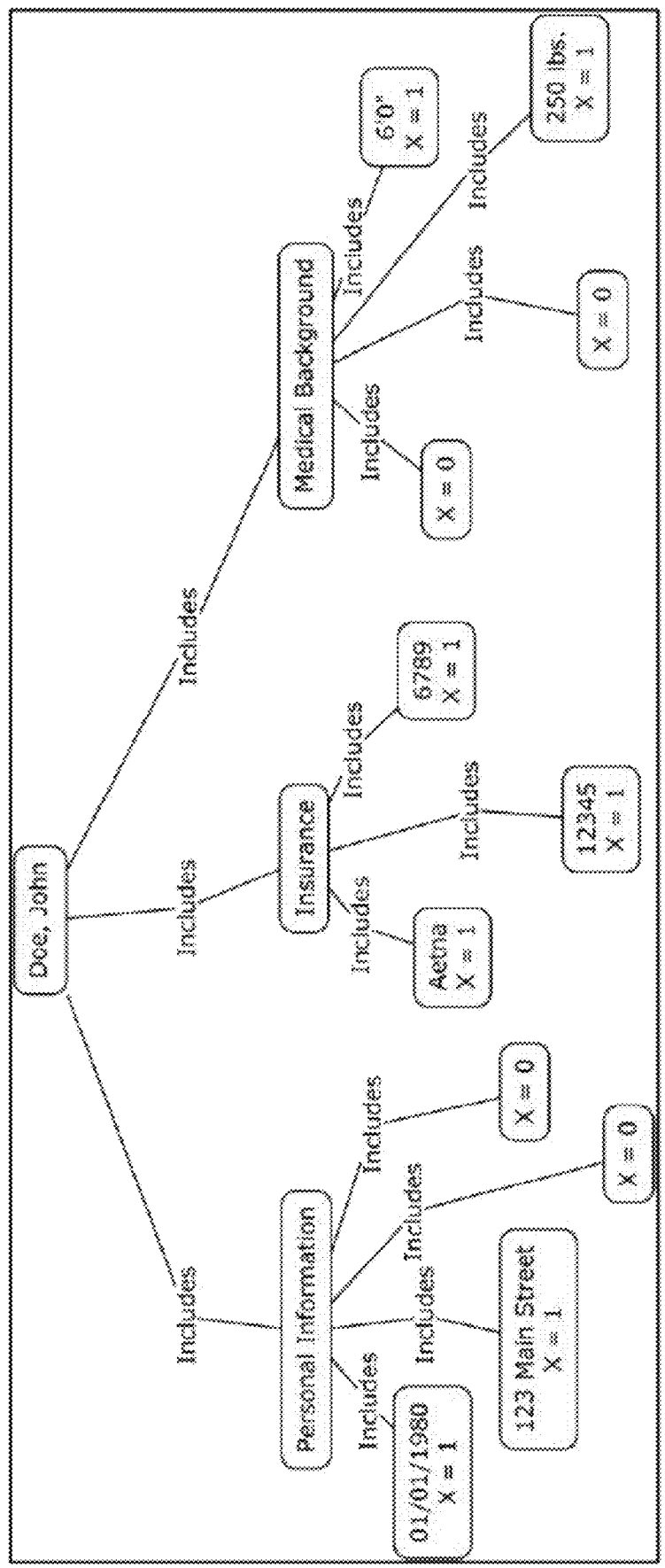
FIG. 7 is a schematic representation of a patient master map with balance scoring in accordance with an embodiment.

Turning to FIG. 6, a sample patient master map for balanced scoring is shown, in accordance with an embodiment. FIG. 7 follows with the sample patient map indicating the Binary Completeness Variable for each field, in accordance with an embodiment. Based on those maps and the scoring equation, the RSS for the sample patient is 64%.

Figure 8:
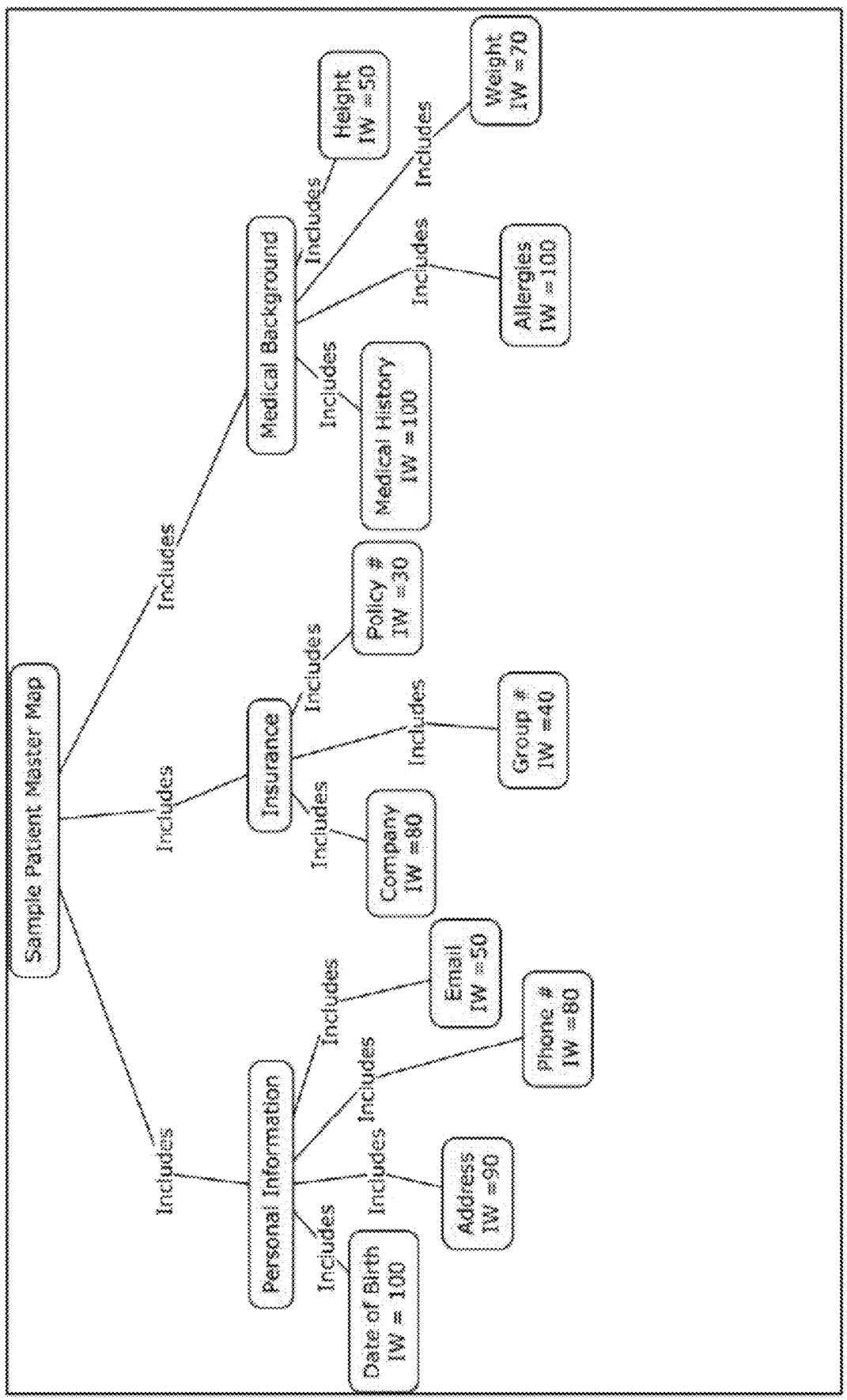
FIG. 8 is a schematic representation of a patient map with balance scoring in accordance with an embodiment.

Table 2, shown below, illustrates IWs for an unbalanced RSS, and FIG. 8 shows the new sample patient master map with modified unbalanced IWs, while the Binary Completeness Variables for the sample patient shown in FIG. 7 remain unchanged, in accordance with an embodiment. The weights used are for purposes of example and have no bearing on actual or perceived relative importance of data fields. Based on those maps and the scoring equation, the RSS for the sample patient is 58%, showing that these new unbalanced IWs make this patient record 'less complete'.

TABLE 2

Unbalanced Importance Weights for Sample Patient

| Data Field | Importance Weight |
| --- | --- |
| Date of Birth | 100 |
| Address | 90 |
| Phone # | 80 |
| Email | 50 |
| Insurance Company | 80 |
| Insurance Group # | 40 |
| Insurance Policy # | 30 |
| Medical History | 100 |
| Allergies | 100 |
| Weight | 70 |
| Height | 50 |

While there appears to be no certain answer for an optimal scoring algorithm that can take into account various preferences for the importance of individual patient record data fields, implementing the RSS scoring equation in DCAP allows for the score to be tailored to the needs of the user because it is dynamic and modifiable. Further development and use of DCAP can also lead to discoveries in better scoring algorithms, and the possibilities with those improvements are elaborated upon later in this disclosure.

Another important metric to establish is the Patient Database Score (PDS), which defines the overall strength of all records in the database and is the average of the various RSS scores (Equation 2).

$$PDS(\%) = \frac{RSS_1 + RSS_2 + \ldots + RSS_n}{n} \quad (2)$$

where $RSS_n$ is a Record Strength Score (Total Strength of Completeness for Individual Patient Record constrained from 0 to 100%) for $i^{th}$ patient; and n is the total number of patient records.

This metric allows for comparisons between databases to determine better record keeping software packages and strategies. Furthermore, using database segmentation techniques, subpopulations of patient records can be compared using the Patient Subgroup Score (PSS), which averages the RSS scores of the patients of interest by age, race, gender, and insurance status, for example, and can allow for an in depth analysis of record strength based on patient information (Equation 3). This topic is further elaborated upon later in this disclosure.

$$PSS(\%) = \frac{RSS_1 + RSS_2 + \ldots + RSS_n}{n} \quad (3)$$

where $RSS_n$ is the Record Strength Score (Total Strength of Completeness for Individual Patient Record constrained from 0 to 100%) for $i^{th}$ patient that meets a subpopulation condition; and n is the total number of patient records that meet subpopulation condition.

Individual data fields across the patient database can also be compared using the Data Field Completeness Score (DFCS), which averages the binary completeness variable of a specific data field across all (Equation 4), or a subgroup of (Equation 5), patients to determine how well one particular class of data is being recorded. The DFCS allows for comparisons across databases and subgroups to ensure proper patient record keeping for each data field. The various scores and terms of importance in scoring are summarized in Table 3, below.

$$DFCS(\%) = \frac{\sum_{1}^{N} X_{iK}}{n} \times 100 \quad (4)$$

Where $X_{ik}$ is a Binary Completeness Variable for $i^{th}$ patient (1 represents complete data field, 0 represents incomplete) and $k^{th}$ data field, where k remains constant and i iterates for individual patients; and n is the total number of patient records.

$$DFCS_k(\%) = \frac{\sum_{1}^{N} X_{iK}}{n} \times 100 \quad (5)$$

Where $X_{ik}$ is a Binary Completeness Variable for $i^{th}$ patient (1 represents complete data field, 0 represents incomplete) and $k^{th}$ data field, where k remains constant and i iterates for individual patients that meet the subpopulation condition; and n is the total number of patient records that meet subpopulation condition.

TABLE 3

Summary of Various Scores Produced by DCAP

| Metric | Definition | Description | Example |
| --- | --- | --- | --- |
| Record Strength Score (RSS) | See Equation 1 | Measures the strength of an individual patients record | Mr. John Doe's record has a 70% RSS score |
| Patient Database Score (PDS) | See Equation 2 | Measures the strength of the entire patient record database at a health care center | XYZ Medical Center's PDS Score is 50% |

TABLE 3-continued

Summary of Various Scores Produced by DCAP

| Metric | Definition | Description | Example |
| --- | --- | --- | --- |
| Patient Subgroup Score (PSS) | See Equation 3 | Measures the strength of the patient records of a specific population of the patients seen by the health care center | The PSS Score of male patients over the age of 55 is 95% |
| Data Field Completeness Score (DFCS) | See Equation 4 for database See Equation 5 for subpopulation | Measures the strength of recording for a specific data field for either all patients in a database or a subset of patients | The DFCS for Insurance Policy Number is 80% The DFCS for height among females is 86% |

Experimentation with Hypothetical Data

In order to build and test DCAP, first a random population set was generated in Excel® using the same fields as shown in FIGS. 2 and 3. The Excel random function was used to introduce random missing fields and the file was converted into a CSV format to be used by DCAP. In terms of specific mechanics of a DCAP embodiment itself, DCAP is programmed and/or configured to read in three CSV files: (1) Patient File—These are each of the patients records in one CSV, with columns representing fields and rows representing individual patients; (2) Template File—These are all of the field labels (one row with multiple columns matching in order to the fields stored in the patient file); and (3) Importance Weight File—These are the importance weight corresponding to the template file.

DCAP is then programmed and/or configured to take these files, convert them to arrays, check for completeness against a defined String variable that indicates incompleteness which can range from a first character indicator to a blank value, and then output the general result of the PDS for the entire database and RSS for each patient. Each of the metrics, PDS and RSS, are also calculated for balanced IWs so that one can compare a simple average to the average weighted by user IWs in the Importance Weight file. DCAP is also programmed and/or configured to automatically generate the DFCS for each field. FIGS. 9 and 10 show samples of this DCAP result printout, with FIG. 9 showing a sample hypothetical patient DCAP result part 1 and FIG. 10 showing a sample hypothetical patient DCAP result part 2.

Figure 11:
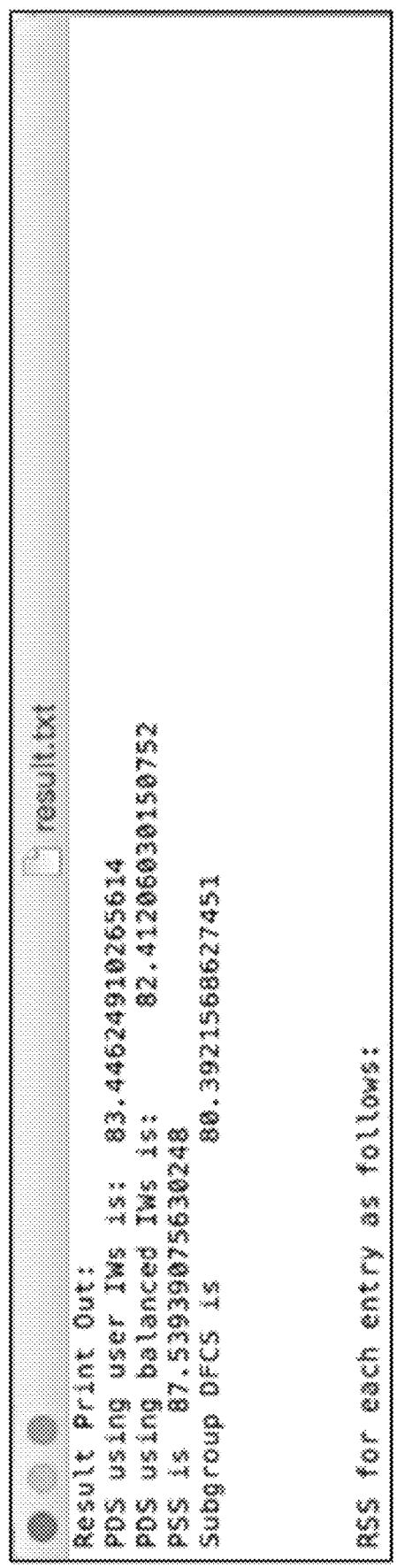
FIG. 11 is a representation of a patient result from hypothetical data with PSS and subgroup DFCS scores document in accordance with an embodiment.

Another aspect of DCAP involves further user input to generate PSS scores and subfield DFCS scores. First, after DCAP has generated the data mentioned previously, it can be programmed and/or configured to ask a user whether they would like to generate a PSS or subfield DFCS score. If yes, the user can then select a field and then indicate whether the search inside the field will be an exact text bound or a numerical range. In the case of text bound, patients that will meet the population criteria must have an exact match to the subfield name. For numerical bound, patients that meet the population criteria must be within the lower and upper bound as indicated by the user. Upon specifying the population of interest's parameters, DCAP can be programmed and/or configured to generate the PSS for this subpopulation. It will then be programmed and/or configured to ask the user whether they would like a DFCS score for that subpopulation. If yes is selected, DCAP will be programmed and/or configured to ask for the field and then the DFCS for that subpopulation will generate. FIG. 11 provides a sample patient result for the hypothetical data where PSS and subgroup DFCS were generated. The subpopulation for the sample shown in FIG. 11 includes patients between the age of 0 and 50 and the DFCS field is race.

In order to test DCAP on real patient data, de-identified data from the Health care Cost and Utilization Project (HCUP) was used, specifically the State Inpatient Database (SID) with 2012 data from Florida.

Due to the size of the data set, over 2 million entries, one thousand records were randomly extracted in order to test DCAP. Incomplete or missing data was determined based on the guide provided by HCUP data, usually blank spaces in the CSV file. In setting the importance weights, it was noted that many fields were used to handle excess information. For example, there are 31 fields for up to 31 diagnoses, so having a blank in some of those fields is not actually resultant of missing information; therefore, the IWs were adjusted to 0. Otherwise, importance weights were set first to balanced and then based on general view of importance. Due to the large number of data variables contained in the HCUP data, the IWs have been omitted for practical purposes.

Figure 12:
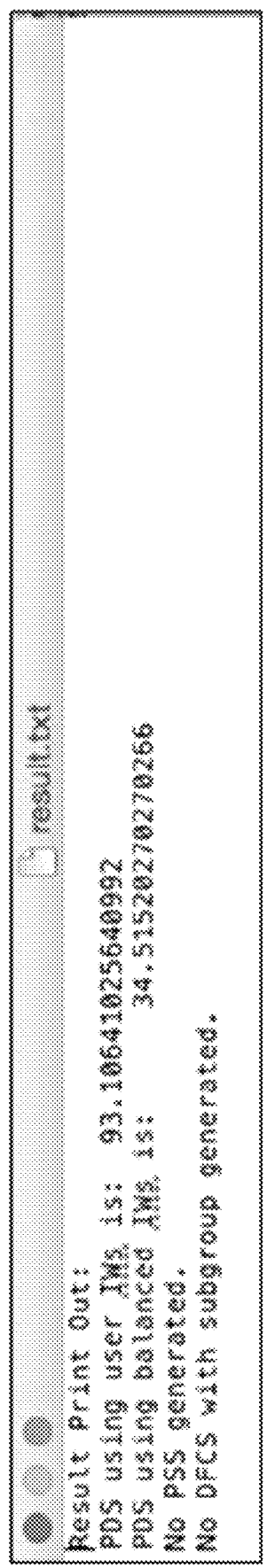
FIG. 12 is a representation of results of HCUP data for balanced IWs document in accordance with an embodiment.
Figure 13:
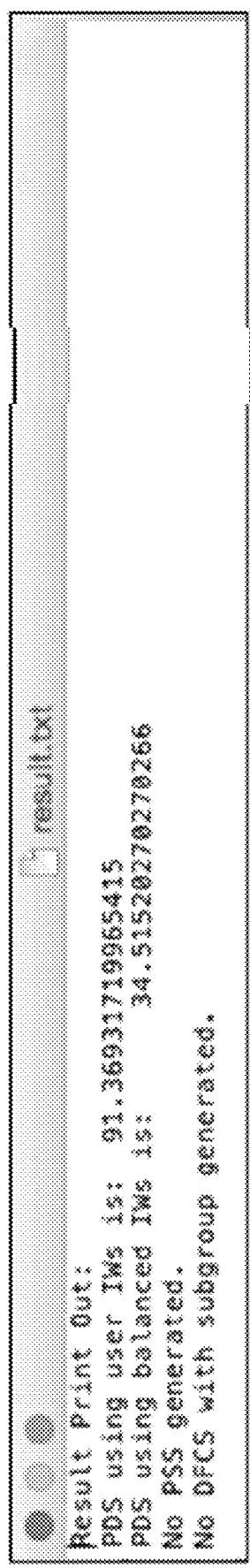
FIG. 13 is a representation of results of HCUP data for unbalanced IWs document in accordance with an embodiment.

Turning to FIGS. 12 and 13, the results of the HCUP data for the balanced IWs and unbalanced IWs respectively, are shown in accordance with an embodiment. The PDS generated with 'balanced IWs' in the result print out incorporates fields as mentioned above such as multiple diagnosis codes, and thus are not a good measure of record completeness. This simple analysis of HCUP SID data in Florida shows that (1) data is not complete to a level necessary for proper recording of health care service, and (2) when the importance of various fields is taken into consideration that measure becomes even weaker. This data and the functionality provided by DCAP allows for multiple areas of further exploration that are discussed later in this disclosure.

Further features of the present invention include automated veracity of patient health care data through data heuristics or through communication with a central database as a cross-reference. Furthermore, IWs can be made less subjective and more objective based on a panel of health professionals to ensure that the completeness of a database is an objective measure based on widely agreed upon standards.

Limitations in access to current clinical data stored in proprietary software packages led to lack in actual testing against various health care databases, but the DCAP tool provides promise in its adaptability to various data sets and data elements. Overall, this disclosure describes the use of real data to show the current problem of incomplete patient data and the importance of creating systems to ensure a high standard of data completeness. In its development and limitations, it also builds a foundation to explore further areas of interest and advocates work committed to making sure that important patient data is complete and accurate.

Managing Chronic Illness Health Care Records

Some embodiments of the present invention are adapted to manage chronic illness health care records. To understand the embodiments of the present invention that manage chronic illness health care records, it is important to have a general understanding of chronic illnesses.

Chronic illnesses generally include conditions that lasts 12 months or longer. Some indications of chronic illnesses include conditions that limit the patient's ability to care for him/herself, affect the ability to live independently, and affect social interactions. Other indicators include a need for ongoing medical products, services, and/or special equipment. Non-limiting examples of chronic illnesses/conditions include kidney disease, diabetes, heart disease, diabetes, most forms of mental illness, hypertension, and congenital anomalies.

Classification and Diagnosis of Chronic Illnesses

Chronic illnesses are typically characterized by both qualitative and quantitative measures. Medical providers record all subjective and objective details during a visit and use all the available information to arrive at an assessment and develop a plan. The assessment for chronic illnesses typically involves assigning a classification or stage of the illness.

These classifications are well-established in the literature and are used universally among medical providers. For example, Chronic Kidney Disease (CKD) is staged 1-5 universally as shown in Table 4.[12] These stages are based on estimated Glomerular Filtration Rate (GFR) which gives an accurate assessment of kidney function to determine clinical progression of disease.

TABLE 4

CKD Staging Criteria
Stages of CKD

| Stage | Description | GFR (mL/min/1.73 m$^2$) |
|---|---|---|
| 1 | Normal kidney function | 90 or higher |
| 2 | Mild loss of function | 60-89 |
| 3a | Mild-moderate loss of function | 45-59 |
| 3b | Moderate-severe loss of function | 30-44 |
| 4 | Severe loss of function | 15-29 |
| 5 | Complete kidney failure | Less than 15 |

The progression of symptoms and other disease variables may also be used in addition to classifying chronic diseases. There are general indicators that can be used to predict outcomes and quality of care. These may be symptoms or values gathered in the form of vital signs or laboratory results. For example, creatinine clearance was found to be a significant indicator for clinical outcomes in values less than 30 mL/min.[13]

Diagnosing chronic illnesses is a complex process in which various sources of data may be used. Some diagnoses, such as CKD, are diagnosed and staged mainly using laboratory data and patient information to calculate a metric such as GFR.[14] Other diagnoses, such as hypertension, can be staged using historical vital sign values.[15] Alternatively, chronic illnesses can be diagnosed primarily using subjective data using provider narratives and physical exams, such as dementia.[16] In addition, these diagnoses and staging can vary in terms of what is listed in diagnosis coding, provider problem lists, and narrative diagnoses within the EMR.

Given the complexity of trying to understand chronic illnesses within the context of EMR data analysis, Congestive Heart Failure (CHF) is used herein as a prime example of the intricate interaction between objective laboratory data, objective radiologic imaging interpretations, objective vital signs, subjective provider narrative information, and clinical judgment. The classification of CHF in general clinical practice has largely been on the basis of symptomatic presentation. The NYHA uses a 4-point scale to grade CHF based on the functional capacity of the patient with an emphasis on distinguishing the presence of symptoms at rest or during physical activity.[17] The purpose of this scale is to provide physicians a convenient way to characterize heart failure based on clinical presentation. Functional capacity is assessed by determining a patient's limitations during physical activity due to the presence of symptoms, as shown in Table 5 with the NYHA classification of CHF.[18]

TABLE 5

NYHA Heart Failure Stages
NYHA Functional Classification

| Stage 1 | No limitations on physical activity | Normal activity does not cause symptoms |
|---|---|---|
| Stage 2 | Slight limitation on physical activity | Comfortable at rest; ordinary activity causes symptoms |
| Stage 3 | Marked limitation on physical activity | Comfortable at rest; less than ordinary activity causes symptoms |
| Stage 4 | Unable to carry out physical activity without discomfort | Symptoms at rest. Any physical activity causes increase in discomfort |

This clinical assessment and classification approach would provide a way to determine if the patient requires further treatment.

The AHA staging of heart failure is a similar scale that evaluates the extent of a patient's symptoms and functional capacity in the context of underlying structural disease, as seen in Table 6.19

TABLE 6

AHA Heart Failure Stages
AHA Stages of Heart Failure

| Stage A | High risk of developing heart failure. No functional or structural disease |
|---|---|
| Stage B | Structural disease. No symptoms present |
| Stage C | Previous or current symptoms of heart failure with underlying structural disease. Controlled with medical treatment |
| Stage D | Advanced disease requiring inpatient support, transplant, or palliative care |

When using this scale, patients do not regress to previous stages due to the presence of structural disease that has little capacity to improve. Thus, there is a clear indication in errors when recording AHA stages in EMRs.

Unfortunately, these scales have their limitations and cannot objectively measure progression of CHF. As such, using the NYHA or AHA scales to trend and map the course of CHF using EMR is not practical. The use of ejection fraction (EF) as a metric for staging heart failure is a more recent method of evaluating the progression of heart failure, as shown in Table 7.[20]

TABLE 7

Heart Failure Staged by Ejection Fraction

| Heart failure with reduced ejection fraction | ≤40% |
|---|---|
| Heart failure with borderline ejection fraction | 41-49% |
| Heart failure with preserved ejection fraction | ≥50% |

Using data about EF is a more objective measure than the other two methods of staging heart failure and is theoretically more practical to use when mapping CHF using EMRs. However, there is a large variability in EF measurements and the measurements can be very imprecise over long-term management.

In the assessment of functional capacity, however, cardiopulmonary indices have become the standard to evaluate heart failure, particularly anaerobic ventilatory threshold (AVT) and maximal oxygen consumption (peak VO2). There is extensive evidence supporting peak VO2 as a strong prognostic in heart failure patients.[21,22] There is also increasing literature that supports AVT and ventricular efficiency (VE) as valuable tools to determine early mortality risk among heart failure patients.[23,24] The results of cardiopulmonary exercise testing can be used as objective values to measure the severity of heart failure as well as the functional status of heart failure patients. Additional monitoring of ventilation and arterial oxygen saturation can also be considered for measuring progression of chronic heart failure.[25] These values can provide excellent indicators of chronic disease and should be considered in the evaluation of heart failure. Unlike the objective measures used for CKD, however, these measures are not exact. While the data from these tests are excellent in following response to treatment, there is little data supporting their use to monitor disease course over the long term.

In terms of monitoring chronic heart failure patients, telecardiology has shown to be effective in reducing cardiac related readmissions as well as improved quality of life among this patient population. This system often involves using home-based cardiac leads sending ECG results to providers who would monitor cardiac function remotely and decide on follow up schedule or assistance using these results.[26,27] However, the use of these monitors to stage CHF is somewhat impractical. Although EKGs provide an excellent snapshot of cardiac muscle function, it would be difficult to stage CHF using a trend in EKGs due to their immense variability.

There is also some evidence suggesting that pro-inflammatory cytokines can be measured to monitor, assess, and predict outcomes for CHF patients.[28] Tumor necrosis factor (TNF)α, interleukin (IL)-10, and IL-6 are the most important cytokines identified in playing a role in the pathogenesis of heart failure. These cytokines play a key role in the remodeling process of the heart, resulting in hypertrophy, death of myocardial cells, and fibrotic changes in cardiac tissue. As a result, cytokines can be important in providing prognostic information about congestive heart failure.[28] Like with the previous measures that have been mentioned, however, these markers are not as useful in the mapping of chronic disease states because of the lack of specificity for heart failure.

Long term management of hypertension also requires staging using objective measures. Mapping this condition via EMRs is very practical due to the ease at which blood pressures can be checked. Table 8 shows the established staging guidelines for hypertension.[29]

TABLE 8

Hypertension Stages (AHA Guidelines)

| Stage | Systolic | Diastolic |
|---|---|---|
| Normal | <120 | <80 |
| Prehypertension | 120-129 | <80 |
| Stage 1 hypertension | 130-139 | 80-89 |
| Stage 2 hypertension | ≥140 | ≥90 |
| Hypertensive emergency | >180 | >120 |

The scale has recently been updated and may be efficiently monitored over the long term. Due to the morbidity associated with hypertension, mapping this disorder may have strong ramifications in public health and clinical management of cardiac disease.

Some other examples of chronic illnesses and their various stages are provided below. Specifically, Glaucoma is provided in Table 9 and Alzheimer's disease is in Table 10.

TABLE 9

Glaucoma

| | |
|---|---|
| Mild/Early Stage | Optic nerve abnormalities consistent with glaucoma, but no visual field abnormalities on any visual field test OR abnormalities present only on short-wavelength automated perimetry or frequency doubling perimetry |
| Moderate Stage | Optic nerve abnormalities consistent with glaucoma and glaucomatous visual field abnormalities in one hemifields AND not within 5 degrees of fixation |
| Advanced/Late/ Severe Stage | Optic nerve abnormalities consistent with glaucoma and glaucomatous visual field abnormalities in both hemifields AND/OR loss within 5 degrees of fixation in at least one hemifield |

TABLE 10

Alzheimer's Disease

| | |
|---|---|
| Mild/Early Stage | Memory loss and other cognitive impairments are minor but become more and more noticeable. The person can compensate for them and continue to function independently |
| Moderate/Mid Stage | Changes become more marked and disabling. Mental abilities decline, personality changes, and physical problems develop. The person becomes more and more dependent on caregivers for daily activities. |
| Severe/Late Stage | Complete deterioration of the personality. Physical problems are dominant with loss of control over bodily functions. The person is totally dependent on others for even the most basic activities. |

While not every chronic illness and its clinical stages/diagnosis guidelines are provided herein, the present invention can be employed to operate with any chronic illness and its corresponding clinical stages/guidelines and in turn the chronic condition matrix for the particular chronic illness, which is based on the guidelines.

Given the various information and clinical judgment that goes into chronic condition diagnoses, developing an EMR system to ascertain accuracy of chronic condition diagnoses is a challenging task. However, the need to provide accurate chronic condition diagnoses and ensure it maintains its veracity temporally through a patient's record is important to ensure a high standard of care. Thus, some embodiments of the present invention are designed based on the issues with chronic condition documentation within EMRs. Embodiments include tracking chronic condition diagnoses across patients, subgroups and databases. Some embodiments handle multiple chronic illnesses and allow for aggregation of tracking across multiple chronic illnesses. Some embodiments account for temporal inconsistencies in diagnoses.

Embodiments of the present invention can provide analytical and statistical outputs to better understand how chronic condition diagnosis data is being recorded, with comparable measures that can determine completeness, consistency, and accuracy when compared to established guidelines. Moreover, the present invention enables health care staff to evaluate the strength of chronic condition data and identify areas of improvement in workflow and records keeping The present invention is vital for clinical practice as many resources in medicine, ranging from provider time, health care systems, data systems, nursing support, pharmacist support, payer systems, and health care research are all linked to chronic care diagnosis data management. Prior to the current invention there were no existing reliable systems that could determine chronic condition diagnosis completeness, consistency, and accuracy. The present invention provides a robust and applicable tool that can help in evaluation of data and provides a foundation for subsequent research in the area that can lead to significant clinical impact.

In addition, the present invention provides a strong analytical and statistical framework to better understand how chronic condition diagnosis data is being recorded using comparable metrics that determine completeness, consistency, and accuracy relative to established guidelines. The tool will ultimately allow health care staff to evaluate the strength of chronic condition diagnosis data and identify areas of improvement in workflow through an intuitive and robust system.

An embodiment of the present invention is referred to as the "Chronic Condition Mapping Package (CCMP)" and includes a tool that is integrated with EMRs, can be a downloaded to work on an EMR platform, or can access patient data or databases, on or connected to an EMR, through an API. In some embodiments, the CCMP is a function of a particular EMR system and can run on the EMR platform.

In order to assess one or more patients' health care data pertaining to chronic illnesses, the present invention needs to identify and retrieve health care records pertaining to chronic illnesses of one or more patients. This can occur through the identification of predetermined code(s), terminology, or acronyms corresponding to chronic illnesses or through data mapping techniques.

Many EMRs systems include known codes for identifying chronic illnesses. For example, some EMR systems use "Chronic Condition Indicators," which categorizes chronic illnesses using ICD-10-CM diagnosis codes. The usage of codes within an EMR system can be used by some embodiments to identify the chronic illnesses and/or the measured or assessed stage of the chronic illness.

When relying on codes, terminology, or acronyms, the present invention may include a lookup table stored in memory which includes a comprehensive list of the various codes, terminology, and/or acronyms that may be used in EMR platforms. The system can then use these lookup tables to identify the chronic illness associated with a particular code, term, or acronym used in a particular EMR platform.

In some embodiments, the present invention is configured to identify information pertaining to chronic illnesses based on an EMR's predetermined input fields. For example, the EMR may include a designated input field, dropdown box, etc. to identify the chronic illness and record the current measured or assessed stage of the chronic illness.

Some embodiments use mapping of the EMR platform/information to identify and retrieve health care records pertaining to one or more of a patient's chronic illnesses. In some embodiments, the present invention uses keywords to identify certain chronic illnesses and then pulls the recorded stage or data used to determine the stage of the chronic illness corresponding to the particular keyword that was recorded in an EMR.

The present invention may use any methods known to a person of ordinary skill in the art to digitally identify chronic illnesses recorded in a patient's health care records and to further identify the corresponding recorded stages of those illnesses. Regardless of the approach to identify the chronic illness and the recorded stage of the illness, the present invention records or retrieves the chronic illness and the recorded stage or data pertaining to the stage of the chronic illness for each encounter for each patient.

To understand the functionality and capability of the tool, it is important to understand the data handling and data analysis features of the present invention.

Data Handling

To understand the evaluation and flow of data through the present invention, some embodiments model patient data stored within the EMR in an intuitive way to map chronic condition diagnosis data. With this aim in mind, an embodiment of the present invention uses concept mapping to visualize the approach to data within the program. This use of concept mapping for EMR data is similar in use to the other programs described herein, such as the DCAP described above.

Figure 14:
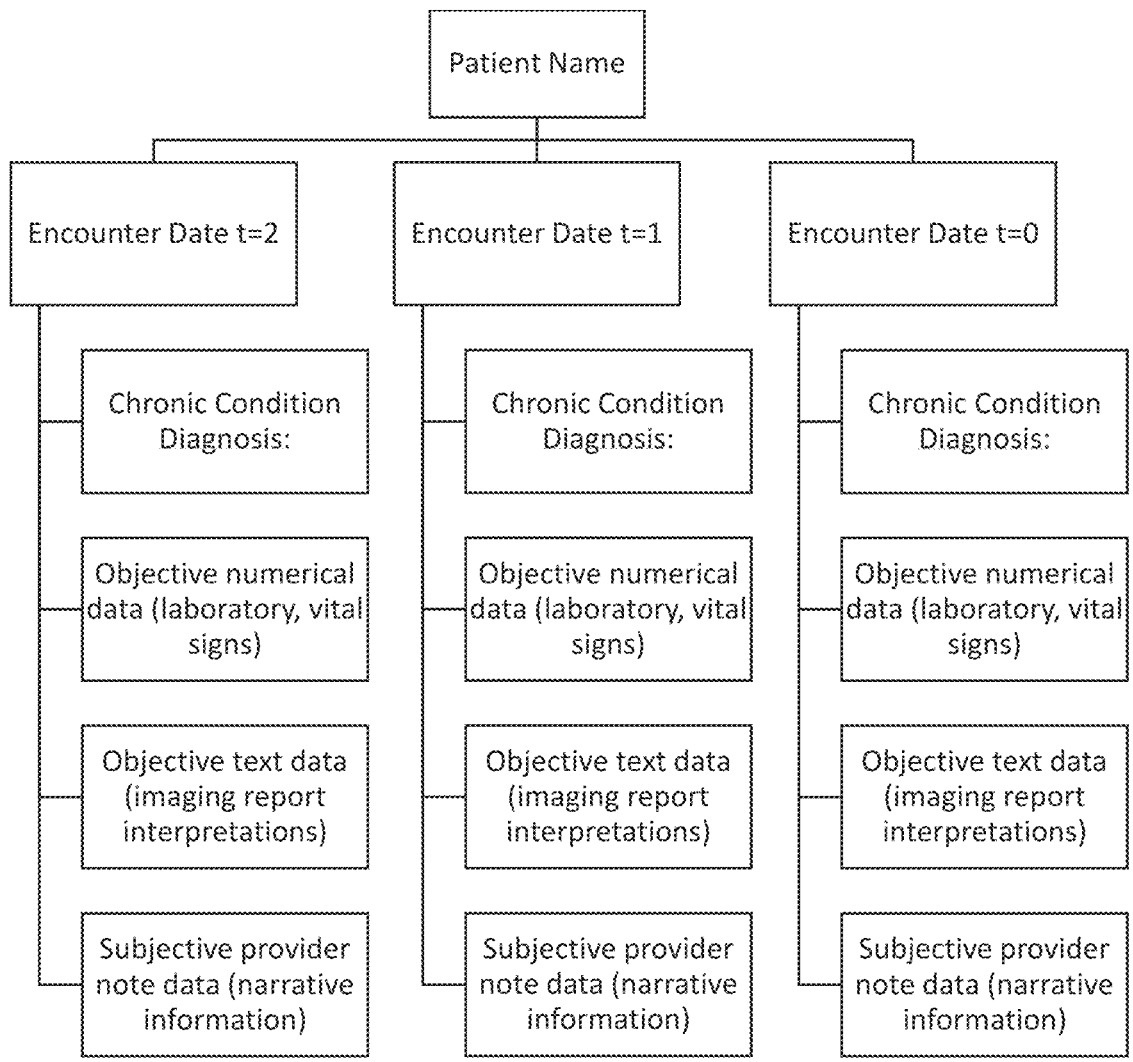
FIG. 14 is an exemplary master concept map version of chronic illness data stored for a hypothetical patient.

FIG. 14 shows an exemplary master concept map version of chronic illness data stored for a hypothetical patient. Specifically, it shows what areas of data are collected and how the data are evaluated. It first starts at the encounter level and is equipped to obtain and evaluate data through multiple encounters. An encounter is an instance in which the health care provider sees the patient and records health care information.

Within an encounter, an embodiment of the present invention determines what chronic condition diagnoses are recorded. As explained above, often, the diagnoses and treatments are recorded using codes. These codes will be checked against previous encounters to determine whether the chronic condition diagnoses list is complete (i.e. are all chronic illnesses that were initially noted still active in the EMR) and whether they are temporally accurate (for chronic illnesses that stage progressively, are the stages recorded during subsequent encounters progressively worse than the stages recorded in previous encounters). From there, some embodiments of the present invention assess other recorded information from the patient's medical chart/electronic health care data to determine the accuracy of chronic condition diagnosis listing. The accuracy is based upon known and generally accepted guidelines such as those found in Tables 4-10.

Some embodiments rely on objective numerical data (such as laboratory values, vital signs and other measurements taken to assess the stage of a chronic illness), objective textual data (such as radiographic interpretations of imaging studies), and/or subjective textual data (such as narrative data from provider notes).

Figure 15:
FIG. 15 is an exemplary master concept map version of chronic illness data stored for a hypothetical patient.

FIG. 15 provides a single diagnosis (CKD) example for evaluation against the master concept map. For this patient, since the onset of the chronic illness diagnosis, subsequent encounters carried on the diagnosis, which were complete and temporally consistent. In the first two encounters, the diagnosis was accurate based upon laboratory (eGFR) guidelines. In the third encounter, however, the diagnosis was inaccurate relative to the guideline suggested stage based upon the eGFR. The stage should have been stage IV based on the recorded eGFR value. As will be explained below, an embodiment of the present invention can use the objective numerical data and calculate the Chronic Condition Guidelines Score, which would confirm that there is a discrepancy in the data. The present invention can then notify the user of the discrepancy in the data, which would alert the user that there is also a discrepancy in the recorded CKD stage.

Figure 16:
FIG. 16 is an exemplary master concept map version of chronic illness data stored for a hypothetical patient.

FIG. 16 provides another example in which multiple chronic illnesses, CKD and CHF, are recorded. In this example, the CKD diagnosis and supporting information remain the same as in the prior example. In the first encounter, the health care provider also records a diagnosis of CHF, which is supported by the subjective narrative data. In the second encounter, the health care provider does not record a CHF diagnosis in the patient's chart and as a result, the chart does not include subjective data for CHF. In the third encounter, the diagnosis of CHF is present and consistent with the subjective data. As will be explained below, an embodiment of the present invention can use the Chronic Condition Mapping Score, which would reveal that there is a discrepancy in the recordation of one of the patient's chronic illnesses. The present invention can then notify the user of the discrepancy. In other words, the present invention can identify the missing diagnosis of CHF in the second encounter. In addition, the present invention is configured to combine the documentation of both CHF and CKD within this patient's chart into an inclusive score.

Figures 17, 18A:
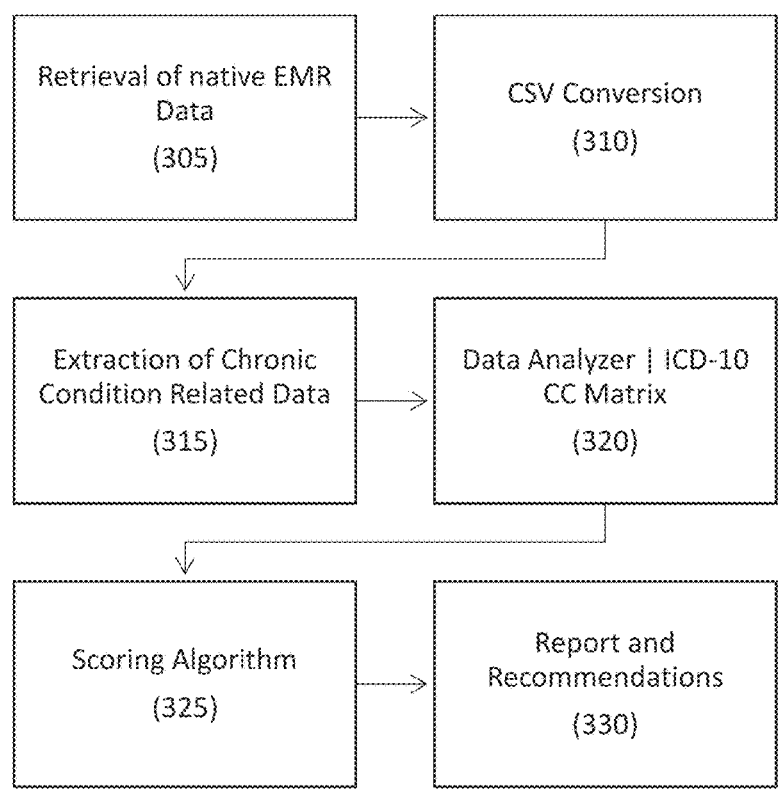
FIG. 17 provides a CSV representation of sample patient data.
FIG. 18A is an exemplary flowchart of an embodiment of the present invention.

For a more concrete visualization of the data, FIG. 17 provides a CSV representation of sample patient data. Specifically, it shows patient encounters based on identifier medical record number (MRN) and encounter date. It also has identifiers, such as age and race that can be used for subgroup amalgamation and multiple diagnosis code entries to accommodate multiple chronic illnesses. In the figure, the term "diagnosis" is abbreviated using "DX" and the diagnosis codes include those codes, such as N181 and I5021, shown in the diagnoses columns. This CSV representation can be carried forward to pertinent data as identified in the concept maps, such as laboratory data, vital signs, radiographic interpretations, and provider narratives. The CSV transformation is one of the manners in which native EMR data can be transformed into a standardized format to allow the system to handle EMR data from different EMRs with different native data formats.

FIG. 18 show the general handling of data for some embodiments of the present invention. The steps provided in the figures and discussed below can be implemented by a computer processor or through any other means described in the "Application" section below. In some embodiments, the present invention initially retrieves or receives native EMR data in step 305. The health care record data can be received or can be retrieved by accessing a database of digital health care record data via a computer network. In some embodiments, the present invention is a tool within a particular EMR and is provided access to the database. In some embodiments, the present invention uses a digital network and APIs to access the databases.

However, much of the health care industry lacks standardization of chronic diagnosis listings, staging, and guidelines. The wide array of information stored in EMRs and their discrepancies in how chronic condition diagnosis information is stored presents a challenge in integrating the present invention into live data to extract the appropriate information. Furthermore, as discussed in the background section, different chronic conditions are diagnosed, staged, and characterized differently. This results in different forms of information being used to determine the diagnosis, including different sources of objective numerical data, objective text-based data, and subjective provider narrative data. In addition, guidelines for diagnosis may differ between providers and institutions which creates another potential barrier for standardization of determining chronic condition diagnosis appropriateness. Thus, some embodiments of the present invention include processes of standardization that allow EMRs to be accurately analyzed within the context of chronic condition diagnosis completeness, consistency, and accuracy.

In some embodiments, the native EMR data is accessed and evaluated using a master concept map to determine the appropriate data to collect. As explained previously, other embodiments may use other methods know to a person of ordinary skill in the art to identify and collect the EMR data for one or more patients in relation to one or more chronic illnesses, including but not limited to using diagnosis codes, keywords, input fields, mapping tables, etc.

As shown in FIG. 18A, the retrieved electronic data can be converted to a standardized CSV file in step 310. While a CSV format is specifically exemplified as one conversion of native EMR data to a standardized format, other embodiments may use other data formats and methods for converting native EMR data to a standardized format.

At step 315, the data pertinent to chronic conditions and the scoring algorithms are extracted. In some embodiments, the pertinent data includes but is not limited to patient ID, encounter dates, first date each chronic illness is recorded, the recorded chronic illness(es), objective numerical data used to determine the stage of the chronic illness(es), objective textual data used to determine the stage of the chronic illness(es), and/or subjective textual data used to determine the stage of the chronic illness(es). The term "chronic condition data" refers to one or more of the following types of data: objective numerical data used to determine the stage of the chronic illness(es), objective textual data used to determine the stage of the chronic illness(es), and/or subjective textual data used to determine the stage of the chronic illness(es).

In some embodiments, the chronic condition data is then analyzed against chronic condition matrices based on guidelines (that can help in temporality and appropriateness of stages) in step 320. A chronic condition matrix is a digital representation of the various stages of a chronic illness and the corresponding chronic condition data for each stage. In some embodiments, the chronic condition matrices clarify the stage of a chronic illness for objective numerical data. In some embodiments, the chronic condition matrices are digital lookup tables or mapping tables similar to tables 4-10 above. Preferably, the present invention will have a chronic condition matrix for each chronic illness.

At step 325, the scoring algorithm is initiated. The scoring output value provides a quantitative comparison of the chronic condition diagnoses management, which was previously not possible. In some embodiments, the calculated score leads to a scoring report that notify health care providers of inaccuracies and can lead to recommendations for changes in workflow of chronic condition data management for a given patient, subgroup, or database. The scoring algorithm may include one or more different scores, which will be explained further below.

The report and recommendations are prepared and electronically sent to the user in step 330. In some embodiments, the report and recommendations are displayed on a graphic user interface upon completion. The display may occur in a new popup window in some embodiments.

Figure 18B:
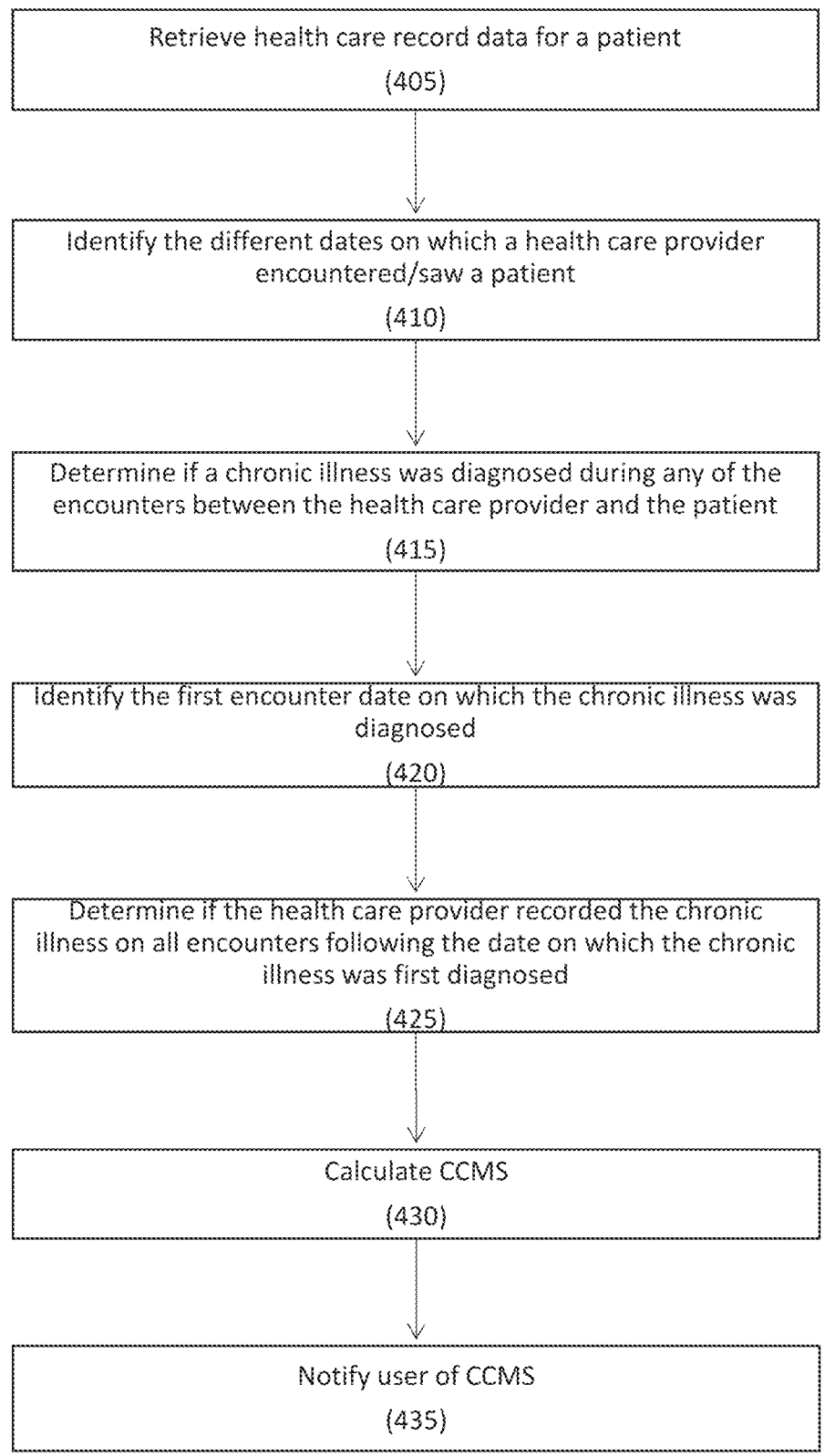
FIG. 18B is an exemplary flowchart of an embodiment of the present invention.

FIG. 18B illustrate a more specific flowchart of an embodiment of the present invention pertaining to the Chronic Condition Mapping Score (CCMS). The CCMS provides a unique approach to quantifying the completeness of a patient's health care data in relation to one or more chronic illnesses.

At step 405, the present invention retrieves a patient's health care record data. As previously explained, the health care record data can be received or can be retrieved by accessing a database of digital health care record data. In some embodiments, the present invention is a tool within a particular EMR and is provided access to the database. In some embodiments, the present invention uses a digital network and APIs to access the databases.

In some embodiments, the patient's health care record data is transformed from the native EMR formats to a standardized format as previously explained in relation to step 310 above. Some embodiments also include the identification and extraction of chronic condition related data. The identification and extraction of this data is achieved by any method known to a person of ordinary skill in the art as explained in relation to step 315 above.

Then, at step 410, the system identifies the different dates on which a health care provider encountered/saw the patient. In some embodiments, the system identifies the different dates for which a patient saw a particular health care provider or health care practice/facility and may categorize the encounter dates based on the identity of the health care provider. In some embodiments, the system identifies the different dates on which a particular patient encountered any health care provider. When searching across multiple health care providers, the system may need to access multiple distinct databases and transform the native format for each database into the standardized format.

Regardless of whether the system is looking across multiple health care providers or a single health care provider, the system determines if a chronic illness was diagnosed/recorded during any of the encounters at step 415. The system identifies different chronic illnesses to determine when each chronic illness was first diagnosed. Then, at step 420, the system determines the first encounter date on which each chronic illness was recorded. This analysis may be performed by any method known to a person of ordinary skill in the art to determine a chronological order for digitally recorded dates.

Once the system identifies the first encounter date on which a chronic illness is recorded, the system, at step 425, analyzes each subsequent encounter to determine if the health care provider recorded the chronic illness on all encounters following the date on which the chronic illness was first diagnosed. This step is performed for each chronic illness found in the patient's digital health care record data. Moreover, the step may be performed across a single health care provider or multiple health care providers.

Once the data is extracted and the chronic conditions are analyzed, some embodiments of the present invention then initiate a scoring algorithm at step 425 during which the Chronic Condition Mapping Score (CCMS) is calculated. The scoring algorithm can be implemented to accurately characterize the chronic condition diagnosis management within an EMR. Specifically, the scoring accounts for the completeness, consistency, and accuracy of the diagnosis of a chronic illness within a patient's digital health care record.

The CCMS is defined in Equation 6 as follows:

$$\text{Chronic Condition Mapping Score } (CCMS) = \frac{\sum_{1}^{N} B_i}{N} \times 100 \tag{6}$$

Where N is the total number of patient encounters since the chronic illness was first recorded, $B_i$ is a binary variable (1 if the chronic illness is recorded and 0 if the chronic illness is not recorded during an encounter) for patient encounter i.

To better understand this score, consider the examples provided in FIGS. 15 and 16. For FIG. 15, the CKD stages are all present in the encounters and temporally consistent. Thus, the CCMS CKD Score for Mr. Smith is 100%. For FIG. 16, the CKD stages are all present and temporally consistent. However, one CHF diagnosis code is missing in the second encounter. As depicted, the other two encounters have the CHF diagnosis code present and temporally consistent. Therefore, Ms. Doe's CCMS CKD Score is 100% and her CCMS CHF Score is 66%.

From here, it is important to understand that the CCMS score can be scaled in two ways. First, for any chronic illness, the CCMS can be determined for a particular patient, for a particular subgroup (e.g., the CCMS CKD Score for all patients between the ages of 40-60), or within the database as a whole. The calculations for the subgroup or database would involve taking the average of the CCMS being studied based on the patients that would be included. Equations 7 and 8 provide a mathematical definition for this scaling:

$$\text{Subgroup } CCMS(SCCMS) = \frac{\sum_{1}^{N} CCMS_i}{N} \times 100 \tag{7}$$

Where CCMS is the CCMS for a specific chronic illness for patient i and N is the total number of patients who meet the subgroup condition.

$$\text{Database } CCMS(DCCMS) = \frac{\sum_{1}^{N} CCMS_i}{N} \times 100 \tag{8}$$

Where CCMS is the CCMS for a specific chronic illness for patient i and N is the total number of patients within the database.

The second way the CCMS score can be scaled is across all chronic illnesses. For example, in Ms. Doe's case (FIG. 16), her combined CCMS (incorporating both her CKD and CHF scores) would be 83%. This combined CCMS can also be scaled along subgroups and databases. Equations 9-11 provide mathematical definitions for these concepts.

$$\text{Total } CCMS \text{ Score } (TCS) = \frac{\sum_{1}^{N} CCMS_i}{N} \times 100 \quad (9)$$

Where CCMS is the CCMS for a specific patient for chronic illness i and N is the total number of chronic conditions.

$$\text{Subgroup } TCS (STCS) = \frac{\sum_{1}^{N} TCS_i}{N} \times 100 \quad (10)$$

Where $TCS_i$ is the TCS for a specific patient i and N is the total number of patients who meet the subgroup condition.

$$\text{Database } TCS (DTCS) = \frac{\sum_{1}^{N} TCS_i}{N} \times 100 \quad (11)$$

Where $TCS_i$ is the TCS for a specific patient i and N is the total number of patients within the database.

Table 11 below provides a list of the CCMS based equations with examples.

Referring back to FIG. 18B, in some embodiments, the CCMS score (and any scores disclosed in the table above) are sent to the user and/or the health care provider at step 430. Some embodiments don't calculate the CCMS score and simply skip to step 430 to send notifications of the existence of discrepancies in recording preexisting chronic illnesses. In some embodiments, alerts/notifications are sent to the proper personnel if the health care provider did not evaluate the patient's chronic condition on all encounters following the date on which a chronic condition was first diagnosed. In some embodiments, alerts/notifications are sent to the proper personnel if the health care provider's evaluation of the chronic illness is temporally inconsistent with previous encounters.

In embodiments in which the system is analyzing a patient's health care record across several health care providers, alerts/notifications are sent to the health care provider that failed to record a chronic illness following the initial encounter in which the chronic illness was recorded. As a result, health care providers that do not have a complete history of a patient's health care records are notified of the patient's preexisting chronic illnesses which could allow the health care provider to follow-up with the patient or modify the treatment to avoid complications that could occur as a result of an unknown preexisting chronic illness.

While the CCMS provides a systematic quantitative analysis for the completeness and consistency of chronic illness diagnoses in EMRs, another score can be calculated to determine accuracy relative to established guidelines.

TABLE 11

Overview of CCMP Scoring Metrics

| Metric | Definition | Description | Example |
| --- | --- | --- | --- |
| Chronic Condition Mapping Score (CCMS) | See Equation 6 | Measures the completeness and consistency of one chronic condition diagnosis for one patient | Mr. Smith has a CKD CCMS of 85% |
| Subgroup CCMS | See Equation 7 | Measures the completeness and consistency of one chronic condition diagnosis for a subgroup of patients | Patients age 60-80 in this database have a SCCMS for CHF of 92% |
| Database CCMS | See Equation 8 | Measures the completeness and consistency of one chronic condition diagnosis for a database of patients | This database has a DCCMS for HTN of 77% |
| Total CCMS (TCS) | See Equation 9 | Measures the completeness and consistency of all applicable chronic condition diagnoses for one patient | Mr. Smith has a TCS of 70% |
| Subgroup TCS (STCS) | See Equation 10 | Measures the completeness and consistency of all applicable chronic condition diagnoses for a subgroup of patients | Patients that are Latino in this database have a STCS of 96% |
| Database TCS (DTCS) | See Equation 11 | Measures the completeness and consistency of all applicable chronic condition diagnoses for a database of patients | This database has a DTCS for of 82% |

More specifically, some embodiments of the present invention include a Chronic Condition Guidelines Score (CCGS) algorithm to determine the accuracy of a patient's recorded health care data relative to established guidelines for chronic illnesses. The CCGS provides a quantitative score to better understand the state of the patient's health care record pertaining to chronic illnesses.

Figure 18C:
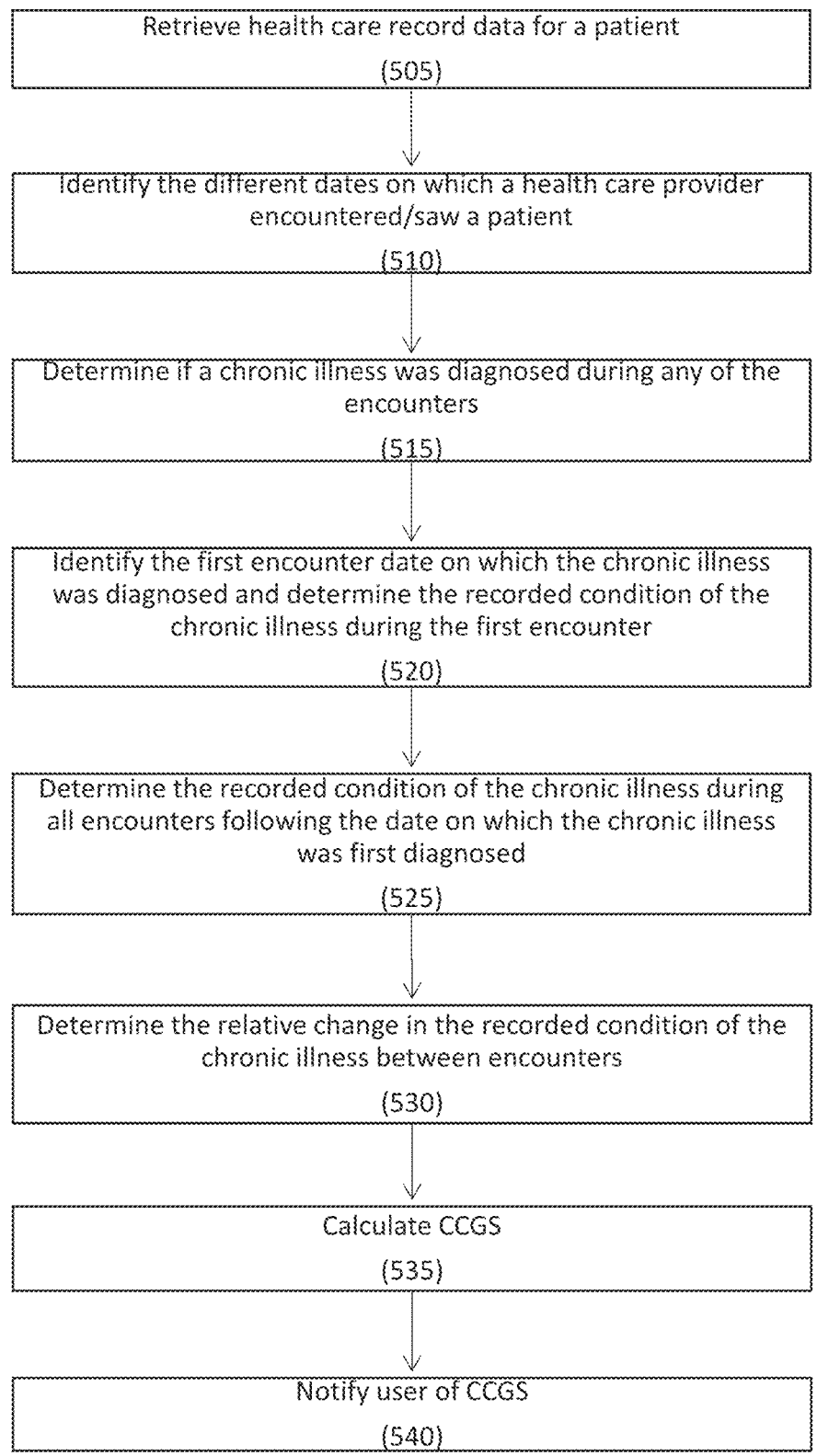
FIG. 18C is an exemplary flowchart of an embodiment of the present invention.

FIG. 18C depicts an exemplary flowchart for an embodiment of the present invention for determining the accuracy of a patient's chronic illness health care data relative to established guidelines and providing a CCGS. As depicted, an embodiment of the present invention includes a method of determining the accuracy of a patient's recorded health care data relative to established guidelines for chronic illnesses and provide a quantitative score to better understand the state of the patient's health care record pertaining to chronic illnesses. Steps 505-515 are generally the same as those steps described in relation to steps 405-415 and 305-315. To succinctly reiterate, in step 505, the system retrieves health care record data for a patient. In step 510, the present invention identifies the different dates on which a health care provider encountered/saw a patient, and in step 515, the present invention determines if a chronic illness was diagnosed during any of the encounters.

If a chronic illness was diagnosed during an encounter, the system identifies the first encounter date on which the chronic illness was recorded, and then the system determines the recorded stage of the chronic illness during said first encounter in step 520. To determine the stage of the chronic illness, an embodiment of the present invention identifies chronic condition data, which may include one or more of the following types of data: objective numerical data corresponding to the chronic illness(es) as recorded by the health care provider, objective textual data corresponding to the chronic illness(es) as recorded by the health care provider, and/or subjective textual data corresponding to the chronic illness(es) as recorded by the health care provider. In some embodiments, only objective data is used by the present invention to determine the stage of the chronic illness. In some embodiments, only objective numerical data is used to determine the stage of the chronic illness.

In some embodiments, the chronic condition data is then analyzed against chronic condition matrices based on guidelines for the chronic illness. The chronic condition matrix provides a digital representation of the various stages of a chronic illness and the corresponding chronic condition data for each stage. In some embodiments, the chronic condition matrices clarify the stage of a chronic illness for objective numerical data. In some embodiments, the chronic condition matrices are digital lookup tables or mapping tables similar to tables 4-10 above. Preferably, the present invention will have a chronic condition matrix for each chronic illness.

In some embodiments, the system identifies the stage of the chronic illness based on a direct recorded identification of the condition/stage of the chronic condition as provided in the EMR platform, and in turn, included in the patient's health care record data.

After the present invention determines the stage of the chronic illness for each encounter, the present invention determines if the recorded stages are temporally accurate. In determining temporal accuracy, the present invention starts with the first encounter and considers whether the condition is recorded in subsequent encounters and determines any changes in the recorded stage of the chronic illness for each subsequent encounter at steps 525 and 530. In some embodiments, the present invention identifies progressions to unhealthier stages as being temporally accurate and progressions to healthier stages as being temporally inaccurate. This logic is employed for chronic illnesses in which there is no ability to recover towards healthier stages. However, the temporal accuracy can be modified based on the chronic illness. If the present invention is tracking a chronic illness in which recovery to healthier stages is possible, then the system can be modified to account for temporal accuracies even when the recorded stage of the chronic illness moves towards a healthier stage with time.

In some embodiments, the present invention calculates a Chronic Condition Guidelines Score (CCGS) at step 535 to convert qualitative patient data into a quantitative measure. The CCGS is calculated for each chronic illness and is defined in Equation 12 below.

$$\text{Chronic Condition Guidelines Score (CCGS)} = \Sigma_1^N (CC_i \times OGV) \quad (12)$$

Where OGV (Objective Guideline Variable) is discrete with the scoring system, and $CC_i$ is a binary variable that has a value of 1 if a chronic condition is recorded and a value of 0 if a chronic condition is not recorded. In some embodiments, the system assumes the initial recorded stage of the chronic condition is accurate and thus the OGV value is 0 for the initial encounter in which the chronic illness is first diagnosed. If the condition/stage of the chronic condition of one of the subsequent encounters is the same as the previous encounter, then the OGV value is also 0. If the diagnosis of the condition of the chronic illness is +/− one stage according to the clinical guidelines/chronic condition matrix, the OGV value is 0.5. To clarify, +/− one stage means 1 stage in a healthier direction or 1 stage in an unhealthier direction. If the diagnosis of the condition of the chronic illness is not within +/− one stage (i.e., 2 or more stages in either the healthier or unhealthier directions) of the previously recorded condition according to guidelines, the OGV value is 1. In some embodiments, the OGV is set to 1 if the chronic illness from previous visit is completely missing.

During a patient visit the health care provider (e.g. attending physician) may identify any number of chronic illnesses (N). The CCGS score is calculated for each visit to ascertain the continuation in the observation and measurement of each chronic illness. As exemplified in FIG. 19, in the absence of a new chronic illness during a subsequent visit the CCGS score for the present visit must be equal to or less than the CCGS score for the previous visit. This condition does not hold true if new chronic illness(es) are identified during the present visit. Thus, an embodiment of the present invention must identify the first encounter in which each chronic illness is recorded.

The CCGS is calculated for each visit for one or more chronic illnesses. The present invention looks for instances in which the CCGS of a subsequent visit is more than the CCGS of a previous visit. If this occurs, the system recognizes that there is a discrepancy and can notify the user.

As an example, consider Patient A who is diagnosed with Alzheimer's disease on visit $V_1$. However, the disease is not recorded for the subsequent visit $V_2$. Then, the disease is recorded again during a third visit $V_3$. In this case, CCGS $(V_3)$ would be set to 1 and as a result, CCGS$(V_3)$>CCGS $(V_2)$<CCGS$(V_1)$ assuming that no other chronic illnesses were recorded during the visits. This situation can trigger an alarm within the system that there is a possibility that one or more of the chronic conditions were not recorded adequately.

As another example, consider Patient X has been diagnosed with type 1 diabetes and was newly diagnosed with Chronic Kidney Disease (CKD) stage 1 as recorded during initial visit $V_1$. Incidentally, the diagnosis of CKD stage 1 was not recorded during the subsequent visit $V_2$ although the prevalence of type 1 diabetes was recorded. Then, during a third visit, $V_3$, CKD stage 1 and diabetes stage 1 were recorded. In this case, CCGS($V_3$) would be set to 1 because CKD was not diagnosed during $V_2$ and a result, CCGS($V_3$)>CCGS($V_2$)<CCGS($V_1$). As a result, the system triggers an alarm in the system.

This scoring system allows for chronic condition diagnosis data to be evaluated for completeness, consistency, and accuracy. Furthermore, CCGS scales in the same way as CCMS. Namely, it can be determined for one condition for a specific subgroup or the database (SCCGS and DCCGS, respectively). It can also be combined across chronic conditions (TGS), and the TGS score can be combined across subgroups or databases (STGS and DTGS, respectively).

CCGS and CCMS can also be compared to each other to determine differences in accuracy alone (having already accounted for completeness and consistency). This is important in that guidelines may change or not be universally agreed upon, or the entity sourcing the data may be using a different accuracy guideline. Having both scores reported provides flexibility and utility that would be lost in a combined score.

In some embodiments, at step 540, an alert/notification is sent to a user, such as a health care provider, to notify the user of the CCGS score. In some embodiments, an alert/notification is sent to a user prior to calculating the CCGS score or without having calculated the CCGS. In some embodiments, an alert/notification is sent to a user if the stage of the chronic illness of a subsequent encounter is clinically healthier than a recorded stage of the chronic illness during a prior encounter. In some embodiments, an alert/notification is sent to a user, such as a health care provider, if the stage of the chronic illness of a subsequent encounter is more than a predetermined number of stages (e.g. more than 1 stage) away from the recorded stage of the chronic illness during a prior encounter. In some embodiments, an alert/notification is sent to a user, such as a health care provider, if the stage of the chronic illness changes between encounters.

EXPERIMENTATION

Figures 19, 20:
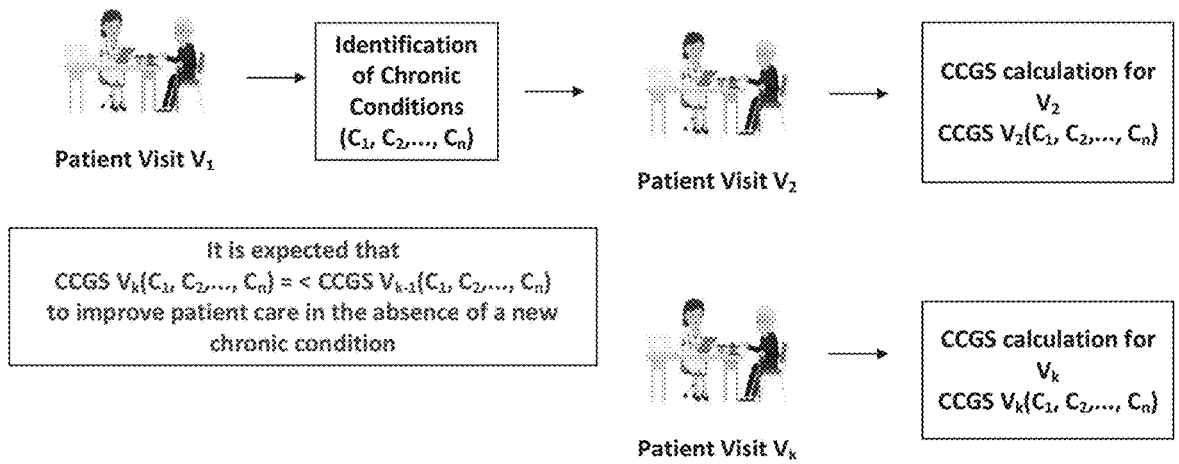
FIG. 19 is a schematic detailing the calculation of CCGS for each visit and the expected outcome of those values.
FIG. 20 shows an exemplary command line entry of parameters into present invention.

In order to develop and test the present invention, a random population of patient and encounters were generated using an Excel file and in-program random number generation. Specifically, the same fields were used as in FIG. 17 along with a column of Estimated Glomerular Filtration Rates (eGFR) to test CCGS for CKD. FIG. 20 shows the command line entry of parameters into present invention, while FIG. 21 shows a sample results page with metrics.

Once PCAP obtains the patient encounters file, it first converts them into arrays. Specifically, it first parses out individual patients and orders encounters within patient arrays based on date (ensuring that the first encounter analyzed is the oldest). Starting with the oldest encounter, it begins storing iterations of chronic condition diagnosis coding using a diagnosis code matrix. In this reference matrix, ICD-10 codes are assigned a binary variable to indicate whether they are or are not a chronic condition. Furthermore, the matrix also stores possible preceding diagnosis codes within the chronic condition to ensure temporal consistency of the diagnosis listed in each encounter. PCAP then analyzes each subsequent encounter, creating new iterations for new chronic conditions, and evaluating an existing list of chronic conditions to ensure completeness and consistency, allowing for generation of the CCMP scores (CCMS and CCGS). Using CKD as the sample example, eGFR guidelines are used to determine predicted CKD stages and compared to listed stages to generate CCGS scores.

Testing with this hypothetical data was important to determine accurate scoring results from CCMP as well as to ensure that the framework and functionalities of the program were robust. After verifying accuracy through manual calculation analysis in Excel, CCMP was confirmed to produce successful results.

Based on the stated objectives, the tested CCMP was successful in determining chronic condition diagnosis completeness, consistency, and accuracy. It provides a mechanism for data processing and analysis that ultimately produces metrics that can be used as a basis for comparison between different patients, subpopulations, and databases. Ultimately, it provides both a conceptual and discrete foundation for analysis of databases and live EMRs with the goal to better understand chronic condition diagnosis data and identify areas of improvement in workflow that can improve health care systems for all parties involved.

As with any statistical analysis, there are limitations in how data is analyzed within the present invention. While the scoring algorithms used are versatile and informative, they may lead to some issues in particular instances. For example, not all chronic conditions have the same impact, so an argument could be made that there should be weighted scoring metrics that take into account the impact of the chronic condition diagnosis before combining scores. Another example of this is using guidelines as part of the diagnosis accuracy. Not all guidelines have the same credence and universal acceptability which would undermine the scores that they would generate. Thus, certain embodiments may use alternative equations and statistical analyses to generate quantitative outputs. Regardless of the mathematical approach, the present invention is an excellent foundation to analyze data and begin meaningful discussions in how to balance different chronic condition diagnoses in terms of impact (both in EMRs and on patient health) and also provide another basis to reevaluate guidelines.

Some embodiments of the present invention can be implemented to determine chronic condition diagnosis management patterns in institutionalized and real data sets.

In some embodiments, the present invention analyzes chronic condition diagnosis data as it compares to differences in scoring between different diagnoses, which might suggest some trends and areas for further investigation.

In some embodiments, the present invention analyzes chronic condition diagnosis data as it compares between different subpopulations. While data completeness has been analyzed from the perspectives of age, race, and gender in the DCAP, this type of work is also important for chronic condition diagnosis data completeness, consistency, and accuracy.

In some embodiments, the present invention analyzes CCMP scoring algorithms within the context of health outcomes. Specifically, seek to understand whether CCMP and chronic condition diagnosis completeness, consistency, and accuracy lead to any discernable effects on health care outcomes.

In some embodiments, the present invention analyzes CCMP scoring in the context of health care economic benefit, with the end goal being to see whether improvements in CCMP tracked chronic condition diagnosis data management result in overall savings in health care costs.

Application

A "module," as may be used herein, can include, among other things, the identification of specific functionality represented by specific computer software code of a software program that is recorded on a computer readable medium. A software program may contain code representing one or more modules, and the code representing a particular module can be represented by consecutive or non-consecutive lines of code. The computer-executable program instructions of an embodiment of the present invention can comprise any computer-programming language known in the art, including but not limited to C, Java, Python, Perl, ActionScript and JavaScript, among many others.

As will be appreciated by one skilled in the art, aspects of the present invention may be embodied/implemented as a computer system, method or computer program product. The computer program product can have a computer processor or neural network, for example, which carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction performance system, apparatus, or device.

The program code may perform entirely on the user's computer, partly on the user's computer, completely or partly on the thermal printer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flow diagrams/charts/block diagrams/system architecture diagrams in the figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While embodiments of the present invention have been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

REFERENCES

1. Djalali S, Frei A, Tandjung R, Baltensperger A, Rosemann T. Swiss Quality and Outcomes Framework: Quality Indicators for Diabetes Management in Swiss Primary Care Based on Electronic Medical Records. Gerontology. 2014; 60(3):263-273.
2. Nasir A, Gurupur V, Liu X. A New Paradigm to Analyze Data Completeness of Patient Data. Appl Clin Inform. 2016; 7(3):745-764. Published 2016 Aug. 3. doi:10.4338/ACI-2016-04-RA-0063
3. Nasir, A., Liu, X., Gurupur, V., & Qureshi, Z. Disparities in patient record completeness with respect to the health care utilization project. Health Informatics Journal. 25(2); 401-416. Published 2017 Aug. 8. doi.org/10.1177/1460458217716005
4. Wagner E H. Chronic disease management: what will it take to improve care for chronic illness? Effective Clinical Practice. 1998 August-September; 1(1):2-4.
5. Stuart M E. Public health issues in the development of centralized health care databases. J Public Health Manag Pract. 1995 Winter; 1(1):57-62.
6. Falck L, Zoller M, Rosemann T, Martinez-Gonzlez N A, Chmiel C. Toward Standardized Monitoring of Patients With Chronic Diseases in Primary Care Using Electronic Medical Records: Systematic Review. JMIR Med Inform. 2019; 7(2):e10879. Published 2019 May 24. doi:10.2196/10879
7. Gee P M, Greenwood D A, Paterniti D A, Ward D, Miller L M. The eHealth Enhanced Chronic Care Model: a theory derivation approach. J Med Internet Res. 2015; 17(4):e86. Published 2015 Apr. 1. doi:10.2196/jmir.4067
8. Jimison H, Gorman P, Woods S, et al. Barriers and Drivers of Health Information Technology Use for the Elderly, Chronically Ill, and Underserved. Rockville (Md.): Agency for Healthcare Research and Quality (U S). 2008 November (175):1-1422.

9. Kaelber D C, Jha A K, Johnston D, Middleton B, Bates D W. A research agenda for personal health records (PHRs). J Am Med Inform Assoc. 2008; 15(6):729-736. doi: 10.1197/jamia.M2547
10. Tenforde M, Jain A, Hickner J. The value of personal health records for chronic disease management: what do we know? Fam Med. 2011 May; 43(5):351-4.
11. HCUP Chronic Condition Indicator. Healthcare Cost and Utilization Project (HCUP). May 2016. Agency for Healthcare Research and Quality, Rockville, MD www.hcup-us.ahrq.gov/toolssoftware/chronic/chronic.jsp.
12. Polkinghorne K R. Controversies in chronic kidney disease staging. Clin Biochem Rev. 2011; 32(2):55-59.
13. Barkhuysen P, de Grauw W, Akkermans R, Donkers J, Schers H, Biermans M. Is the quality of data in an electronic medical record sufficient for assessing the quality of primary care?. J Am Med Inform Assoc. 2014; 21(4):692-698. doi:10.1136/amiajnl-2012-001479
14. Polkinghorne K R. Controversies in chronic kidney disease staging. Clin Biochem Rev. 2011; 32(2):55-59
15. Giles, T. D., Materson, B. J., Cohn, J. N. and Kostis, J. B. (2009), Definition and Classification of Hypertension: An Update. The Journal of Clinical Hypertension, 11: 611-614. doi:10.1111/j.1751-7176.2009.00179.x
16. Rikkert M G M O, Tona K D, Janssen L, et al. Validity, Reliability, and Feasibility of Clinical Staging Scales in Dementia. American Journal of Alzheimers Disease & Other Dementiasr. 2011; 26(5):357-365. doi:10.1177/ 1533317511418954.
17. Nomenclature and Criteria for Diagnosis of Diseases of the Heart and Blood Vessels. JAMA. 1953; 153(9):891. doi:10.1001/jama.1953.02940260115033
18. Athilingam P, D'aoust R, Zambroski C, McMillan S, Sahebzemani F. Predictive Validity of NYHA and ACC/ AHA Classifications of Physical and Cognitive Functioning in Heart Failure. Article.sapub.org. http://article.sapub.org/10.5923.j.nursing.20130301.04.html#Ref. Published 2019. Accessed Sep. 17, 2019.
19. Yancy, C. W., Jessup, M., Bozkurt, B., Butler, J., Casey, D. E., Drazner, M. H., . . . Wilkoff, B. L. (2013). 2013 ACCF/AHA guideline for the management of heart failure: Executive summary: A report of the American college of cardiology foundation/american heart association task force on practice guidelines. Journal of the American College of Cardiology, 62(16), 1495-1539. https:// doi.org/10.1016/j.jacc.2013.05.020
20. Kevin S. Shah, Haolin Xu, Roland A. Matsouaka, Deepak L. Bhatt, Paul A. Heidenreich, Adrian F. Hernandez, Adam D. Devore, Clyde W. Yancy, Gregg C. Fonarow. Journal of the American College of Cardiology November 2017, 24140; DOI: 10.1016/ j.jacc.2017.08.074
21. Stelken A M, Younis L T, Jennison S H, et al. Prognostic value of cardiopulmonary exercise testing using percent achieved of predicted peak oxygen uptake for patients with ischemic and dilated cardiomyopathy. J Am Coll Cardiol. 1996; 27: 345-352.
22. Osman A., Mehra M R., Lavie, C J., Nunez, E., Milani, R. The incremental prognostic importance of body fat adjusted peak oxygen consumption in chronic heart failure. Journal of the American College of Cardiology. 2000; 36(7): 2126-2131. https://doi.org/10.1016/50735-1097 (00)00985-2.
23. Pina, I L., Karalis, D. Comparison of four exercise protocols using anaerobic threshold measurement of functional capacity in congestive heart failure. American Journal of Cardiology. 1990; 65(18); 1269-1271. https:// doi.org/10.1016/0002-9149(90)90989-E
24. Gitt, A. K., Wasserman, K., Kilkowski, C., Kleemann, T., Kilkowski, A., Bangert, M., . . . & Senges, J. (2002). Exercise anaerobic threshold and ventilatory efficiency identify heart failure patients for high risk of early death. Circulation, 106(24), 3079-3084.
25. Janicki, J., Weber, K. Cardiopulmonary exercise testing for evaluation of chronic cardiac failure. American Journal of Cardiology. 1985; 55(2): A22-A31.
26. Scalvini, S., Capomolla, S., Zanelli, E., Benigno, M., Domenighini, D., Paletta, L., Giordano, A. Effect of home-based telecardiology on chronic heart failure: Costs and outcomes. Journal of Telemedicine and Telecare. 2005; 11(1), 16-18. https://doi.org/10.1258/ 1357633054461688
27. Roth A, Korb H, Gadot R, Kalter E. Telecardiology for patients with acute or chronic cardiac complaints: The 'SHL' experience in Israel and Germany. International Journal of Medical Informatics. 2006; 75(9): 643-645.
28. Liu, Mao & Chen, Jian & Huang, Dan & Ke, Jianting & Wu, Wei. (2014). A meta-analysis of pro-inflammatory cytokines in chronic heart failure. Heart Asia. 6. 130-136. 10.1136/heartasia-2013-010484.
29. New ACC/AHA High Blood Pressure Guidelines Lower Definition of Hypertension—American College of Cardiology. American College of Cardiology. https://www.acc.org/latest-in-cardiology/articles/2017/11/08/11/47/mon-5pm-bp-guideline-aha-2017. Published 2019. Accessed Sep. 17, 2019.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

What is claimed is:

1. A method for identifying and conveying recordation and temporal inconsistencies in health care patient data pertaining to chronic illnesses, the method comprising the steps of:

accessing a plurality of distinct digital databases using one or more processors, wherein each digital database includes digital health care data in a native format dependent on a software platform used at each healthcare facility;

transforming native digital health care data stored in the database, using the one or more processors, to a standardized format in which the native digital health care data for at least a first patient is converted into a plurality of parsed data fields;

identifying, by the one or more processors, a chronic illness in the standardized digital health care data for the first patient;

identifying, by the one or more processors, a first health care encounter in which the chronic illness was recorded in the digital health care data for the first patient and determining a recorded stage of the chronic illness as diagnosed in the first encounter and recorded in the digital health care data for the first patient, wherein the stage of the chronic illness resides on a clinical continuum of the progression of the chronic illness;

upon determining the first health care encounter in which the chronic illness was recorded in the digital health care data for the first patient, identifying, by the one or more processors, temporally subsequent health care encounters with respect to the first health care encounter in which the chronic illness was recorded and determining, by the one or more processors, if the chronic illness was recorded in the digital health care data for the first patient for each temporally subsequent health care encounter;

determining, by the one or more processors, if the chronic illness was recorded in the digital health care data for the first patient for each temporally subsequent health care encounter;

as a result of determining that the chronic illness was not recorded in the digital health care data for the first patient for each temporally subsequent health care encounter, generating, by the one or more processors, an incompleteness alert, thereby informing a user that the digital health care data for the first patient is incomplete;

if the chronic illness was recorded in the digital health care data for the first patient for each temporally subsequent health care encounter, determining, by the one ore more processors, each stage of the chronic illness as diagnosed during each temporally subsequent health care encounter and recorded in the digital health care data for the first patient;

determining, by the one or more processors, if the stage of the chronic illness diagnosed for each temporally subsequent health care encounter has changed more than one stage along the clinical continuum in comparison to stages diagnosed for each prior health care encounter; and as a result of determining that the stage of the chronic illness diagnosed for each temporally subsequent health care encounter has changed more than one stage along the clinical continuum in comparison to stages diagnosed for each prior health care encounter, generating, by the one or more processors, a temporal inconsistency alert, thereby informing the user that the digital health care data for the first patient is temporally inconsistent with the clinical continuum of the progression of the chronic illness.

2. The method of claim 1, further including:

calculating a chronic condition mapping score according to the following formula:

$$\text{Chronic Condition Mapping Score} = \frac{\sum_{1}^{N} B_i}{N} \times 100$$

where N is the total number of patient encounters since the chronic illness was first recorded, $B_i$ is a binary variable for patient encounter i, wherein $B_i=1$ if the chronic illness is recorded and 0 if the chronic illness is not recorded during an encounter; and displaying on the graphic user interface the numerical chronic condition mapping score of the digital health care record for the first patient, thereby conveying a quantitative analysis of a completeness of the digital health care record for the first patient pertaining to the chronic illness.

3. The method of claim 1, wherein identifying the chronic illness in the digital health care data for the first patient includes identifying a diagnosis code recorded in the digital health care data for the first patient, accessing a database of diagnosis codes, and determining which chronic illness in the database of diagnosis codes corresponds to the diagnosis code recorded in the digital health care data for the first patient.

4. The method of claim 1, wherein determining the stage of the chronic illness includes:

retrieving objective quantitative data of the chronic illness as recorded in the digital health care data for the first patient;

accessing a digital chronic condition matrix, wherein the chronic condition matrix includes various stages of the chronic illness, each stage categorized by a range of objective numerical data; and determining which stage corresponds to the retrieved objective quantitative data in the digital health care data for the first patient.

5. The method of claim 1, wherein the stage of the chronic illness is determined by a recorded stage of the chronic illness and the clinical continuum of the progression of the chronic illness includes a plurality of stages.

6. The method of claim 1, wherein the stage of the chronic illness is determined by objective quantitative data of the chronic illness and the clinical continuum of the progression of the chronic illness includes objective quantitative data.

7. The method of claim 1, wherein the stage of the chronic illness is determined by objective textual data of the chronic illness and the clinical continuum of the progression of the chronic illness includes objective textual data.

8. The method of claim 1, wherein generating a temporal inconsistency alert occurs if the stage of the chronic illness diagnosed for each temporally subsequent health care encounter is not equal to or not progressively worse on the clinical continuum in comparison to stages diagnosed for each prior health care encounter.

9. A method for identifying and conveying recordation and temporal inconsistencies in health care patient data pertaining to chronic illnesses, the method comprising the steps of:

accessing a plurality of digital databases using one or more processors, wherein each digital database includes digital health care data in a native format dependent on a software platform used at each healthcare facility;

transforming native digital health care data stored in the database, using the one or more processors, to a standardized format in which the native digital health care data for at least a first patient;

identifying a diagnosis code recorded in the standardized digital health care data for at least a first patient;

digitally accessing a database of diagnosis codes, wherein the database of diagnosis codes includes a list of chronic illnesses corresponding to a list of diagnosis codes;

determining the chronic illness corresponding to diagnosis code recorded in the digital health care data for the first patient;

identifying a first health care encounter date on which the chronic illness was recorded in the digital health care data for the first patient;

upon determining the first health care encounter in which the chronic illness was recorded in the digital health care data for the first patient, identifying temporally subsequent health care encounters with respect to the first health care encounter in which the chronic illness was recorded and determining if the chronic illness was recorded in the digital health care data for the first patient for each temporally subsequent health care encounter; and as a result of determining that the chronic illness was not recorded in the digital health care data for the first patient for each temporally subsequent health care encounter, generating and sending an incompleteness alert to a user, thereby informing the user that the digital health care data for the first patient is incomplete.

10. The method of claim 9, further including:
calculating a chronic condition mapping score according to the following formula:

$$\text{Chronic Condition Mapping Score} = \frac{\sum_{1}^{N} B_i}{N} \times 100$$

where N is the total number of patient encounters since the chronic illness was first recorded, $B_i$ is a binary variable for patient encounter i, wherein $B_i=1$ if the chronic illness is recorded and 0 if the chronic illness is not recorded during an encounter; and
displaying on the graphic user interface the numerical chronic condition mapping score of the digital health care record for the first patient, thereby conveying a quantitative analysis of a completeness of the digital health care record for the first patient pertaining to the chronic illness.

11. The method of claim 9, further including:
determining a recorded stage of the chronic illness as diagnosed in the first encounter and recorded in the digital health care data for the first patient, wherein the stage of the chronic illness resides on a clinical continuum of stages coinciding with the progression of the chronic illness;
if the chronic illness was recorded in the digital health care data for the first patient for each temporally subsequent health care encounter, determining each stage of the chronic illness as diagnosed during each temporally subsequent health care encounter and recorded in the digital health care data for the first patient;
determining if the stage of the chronic illness diagnosed for each temporally subsequent health care encounter has changed more than one stage along the clinical continuum in comparison to stages diagnosed for each prior health care encounter; and
if the stage of the chronic illness diagnosed for each temporally subsequent health care encounter has changed more than one stage along the clinical continuum in comparison to stages diagnosed for each prior health care encounter, generating a temporal inconsistency alert, thereby informing the user that the digital health care data for the first patient is temporally inconsistent with the clinical continuum of the progression of the chronic illness.

12. The method of claim 11, wherein determining the stage of the chronic illness includes:
retrieving objective quantitative data of the chronic illness as recorded in the digital health care data for the first patient;
accessing a digital chronic condition matrix, wherein the chronic condition matrix includes various stages of the chronic illness, each stage categorized by a range of objective numerical data; and
determining which stage corresponds to the retrieved objective quantitative data in the digital health care data for the first patient.

13. The method of claim 11, wherein the stage of the chronic illness is determined by a recorded stage of the chronic illness and the clinical continuum of the progression of the chronic illness includes a plurality of stages.

14. The method of claim 11, wherein the stage of the chronic illness is determined by objective quantitative data of the chronic illness and the clinical continuum of the progression of the chronic illness includes objective quantitative data.

15. The method of claim 11, wherein the stage of the chronic illness is determined by objective textual data of the chronic illness and the clinical continuum of the progression of the chronic illness includes objective textual data.

16. A non-transitory computer-readable storage medium containing program code for executing the following steps:
providing remote access to a plurality of databases over a network through a graphical user interface, wherein a digital health care data for the first patient can be stored in a native format dependent on a software platform used by each healthcare facility;
accessing, by one or more processors, the plurality of databases containing the digital health care data for the first patient;
transforming the digital health care data for the first patient from the native format into a standardized format in which the native health care patient record data for one or more patients is converted into a plurality of parsed data fields;
identifying a diagnosis code recorded in the standardized digital health care data for the first patient;
digitally accessing a database of diagnosis codes, wherein the database of diagnosis codes includes a list of chronic illnesses corresponding to a list of diagnosis codes;
determining a chronic illness corresponding to the diagnosis code recorded in the digital health care data for the first patient;
identifying a first health care encounter date on which the chronic illness was recorded in the digital health care data for the first patient;
upon determining the first health care encounter in which the chronic illness was recorded in the digital health care data for the first patient, identifying temporally subsequent health care encounters with respect to the first health care encounter in which the chronic illness was recorded and determining if the chronic illness was recorded in the digital health care data for the first patient for each temporally subsequent health care encounter; and
as a result of determining that the chronic illness was not recorded in the digital health care data for the first patient for each temporally subsequent health care encounter, generating and sending an incompleteness alert to a user, thereby informing the user that the digital health care data is incomplete for the first patient.

17. The non-transitory computer-readable storage medium of claim 16, further including program code for executing the following steps:
determining a recorded stage of the chronic illness as diagnosed in the first encounter and recorded in the digital health care data for the first patient, wherein the stage of the chronic illness resides on a clinical continuum of stages coinciding with the progression of the chronic illness;

as a result of determining that the chronic illness was recorded in the digital health care data for the first patient for each temporally subsequent health care encounter, determining each stage of the chronic illness as diagnosed during each temporally subsequent health care encounter and recorded in the digital health care data for the first patient;

determining if the stage of the chronic illness diagnosed for each temporally sequent health care encounter has changed more than a predetermined number of stages along the clinical continuum in comparison to stages diagnosed for each prior health care encounter; and as a result of determining that the stage of the chronic illness diagnosed for temporally each subsequent health care encounter has changed more than the predetermined number of stages along the clinical continuum in comparison to stages diagnosed for each prior health care encounter, generating a temporal inconsistency alert, thereby informing the user that the digital health care data for the first patient is temporally inconsistent with the clinical continuum of the progression of the chronic illness.

18. The non-transitory computer-readable storage medium of claim 16, further including program code for executing the following steps:

retrieving objective quantitative data of the chronic illness as recorded in the digital health care data for the first patient;

accessing a digital chronic condition matrix, wherein the chronic condition matrix includes various stages of the chronic illness, each stage categorized by a range of objective numerical data; and determining which stage corresponds to the retrieved objective quantitative data in the digital health care data for the first patient.

* * * * *